(12) United States Patent
Cooks et al.

(10) Patent No.: US 11,309,172 B2
(45) Date of Patent: Apr. 19, 2022

(54) REACTION MONITORING

(71) Applicant: Purdue Research Foundation, West Lafayette, IN (US)

(72) Inventors: Robert Graham Cooks, West Lafayette, IN (US); Xin Yan, West Lafayette, IN (US); Christopher Pulliam, West Lafayette, IN (US); Ryan M. Bain, West Lafayette, IN (US); Tawnya Flick, Thousand Oaks, CA (US)

(73) Assignee: Purdue Research Foundation, West Lafayette, IN (US)

(*) Notice: Subject to any disclaimer, the term of this patent is extended or adjusted under 35 U.S.C. 154(b) by 303 days.

(21) Appl. No.: 15/672,862

(22) Filed: Aug. 9, 2017

(65) Prior Publication Data
US 2018/0047552 A1 Feb. 15, 2018

Related U.S. Application Data

(60) Provisional application No. 62/375,927, filed on Aug. 17, 2016, provisional application No. 62/374,146, (Continued)

(51) Int. Cl.
*H01J 49/00* (2006.01)
*H01J 49/16* (2006.01)
(Continued)

(52) U.S. Cl.
CPC ...... *H01J 49/0031* (2013.01); *G01N 33/6848* (2013.01); *H01J 49/0409* (2013.01); *H01J 49/165* (2013.01)

(58) Field of Classification Search
CPC .. H01J 49/0031; H01J 49/0409; H01J 49/165; H01J 49/10; H01J 49/0431;
(Continued)

(56) References Cited

U.S. PATENT DOCUMENTS 8,304,718 B2 11/2012 Ouyang et al.
9,184,036 B2 11/2015 Cooks et al.
(Continued)

OTHER PUBLICATIONS

Yan et al., On-Line Reaction Monitoring and Mechanistic Studies by Mass Spectrometry: Negishi Cross-Coupling, Hydrogenolysis, and Reductive Amination, 2014, Angew. Chem. Int. Ed., 53, 5931-5935. (Year: 2014).*
(Continued)

*Primary Examiner* — Lore R Jarrett
(74) *Attorney, Agent, or Firm* — Brown Rudnick LLP; Adam M. Schoen

(57) ABSTRACT

The invention generally relates to systems and methods for on-line reaction monitoring. In certain embodiments, the invention provides systems that include a reaction vessel having an outlet, a quantitation unit coupled to the outlet and configured to introduce internal standard and solvent into reaction solution flowed from the reaction vessel, one or more ion generating devices that receive flow from the quantitation unit, and a mass spectrometer. In certain embodiments, the invention provides systems for multiple reaction monitoring that include a plurality of reaction vessels, a plurality of ion generating devices, a plurality of channels, each channel coupling a reaction vessel to an ion generating device, an actuator coupled to the plurality of ion generating devices to thereby allow movement of the plurality of ion generating devices, and a mass spectrometer.

10 Claims, 23 Drawing Sheets

Related U.S. Application Data filed on Aug. 12, 2016, provisional application No. 62/372,505, filed on Aug. 9, 2016.

(51) Int. Cl.
*H01J 49/04* (2006.01)
*G01N 33/68* (2006.01)

(58) Field of Classification Search
CPC .. H01J 49/0413; H01J 49/00; G01N 33/6848; G01N 30/7233; G01N 30/16; G01N 30/88; G01N 35/0092; G01N 30/72; G01N 27/62; G01N 35/026; G01N 35/08; G01N 35/00871; G01N 30/8658; G01N 30/06; G01N 2030/067; G01N 2030/8813; G01N 2030/628; G01N 2030/027; G01N 2030/8804; G01N 35/00; G01N 30/02; G06F 19/00; Y10T 436/24

See application file for complete search history.

(56) References Cited

U.S. PATENT DOCUMENTS

| | | | |
|---|---|---|---|
| 2004/0051180 A1 | 3/2004 | Kado et al. | |
| 2013/0280819 A1* | 10/2013 | Cooks | H01J 49/0445 436/173 |
| 2013/0295597 A1* | 11/2013 | DeWitte | G01N 30/06 435/23 |
| 2015/0107679 A1* | 4/2015 | Downie | B01F 15/00207 137/7 |

OTHER PUBLICATIONS

Santos et al., Study of Homogeneously Catalyzed Ziegler—Natta Polymerization of Ethene by ESI-MS, 2006, Angew. Chem. Int. Ed., 45, 977-981. (Year: 2006).*
Amarante, 2009, Bronsted Acid Catalyzed Morita-Baylis-Hillman Reaction: A New Mechanistic View for Thioureas Revealed by ESI-MS(/MS) Monitoring and DFT Calculation, Chem. Eur. J., 15:12460-12469.
Bae, 2000, Arginine-rich Anti-vascular Endothelial Growth Factor Peptides Inhibit Tumor Growth and Metastasis by Blocking Angiogenesis, Biol. Chem., 275:13588-13596.
Boyd, 1993, Quantitative Trace Analysis by Combined Chromatography and Mass Spectrometry Using External and Internal Standards, Rapid Commun. Mass Spectrom., 7:257-271.
Busetti, 2012, Trace analysis of environmental matrices by large-volume injection and liquid chromatography-mass spectrometry, Anal. Bioanal. Chem., 402:175-186.
Cartier, 2002, Utilization of synthetic peptides containing nuclear localization signals for nonviral gene transfer systems, Gene Ther., 9:157-167.
Cerutti, 1985, Short Communication—Importance of Coordinated Immune Stimulation in Experimental Antitumor Treatment, Int. J. Immunopharmacol., 7(5):783-787.
Cervera-Padrell, 2012, Monitoring and Control of a Continuous Grignard Reaction for the Synthesis of an Active Pharmaceutical Ingredient Intermediate Using Inline NIR spectroscopy, Org. Process Res. Dev., 16:901-914.
Chauvatcharin, 1995, On-Line Monitoring and Control of Acetone-Butanol Fermentation by Membrane-Sensor Mass Spectrometry, J. Fermentation and Bioengineering, 79:264-269.
Clegg, 2012, NMR reaction monitoring during the development of an active pharmaceutical ingredient, Analytical Methods, 4:1498-1506.
D. A. F. G. F. Industry:, PAT A Framework for Innovative Pharmaceutical Development, a. Q. A. Manufacturing, Rockville, MD, Sep. 2004.
Drexler, 2015, IR and NMR Reaction Monitoring Techniques for Nucleophilic Addition Reactions: In Situ Monitoring of the Addition of Benzimidazole to a Pyridinium Salt, Org. Process Res. Dev., 19:1119-1127.
Erni, 1982, Liquid Chromatorgraphy Mass Spectromoetry in the Pharmaceutical industry: Objectives and Needs, J. Chromatography, 251:141-151.
Fico, 2007, Miniaturization and Geometry Optimization of a Polymer-Based Rectilinear Ion Trap, Anal. Chem, 79:8076-8082.
Foley, 2013, Online NMR and HPLC as a Reaction Monitoring Platform for Pharmaceutical Process Development, Anal. Chem., 85: 8928-8932.
Gaczynska, 2003, Proline- and Arginine-Rich Peptides consititute a Novel Class of Allosteric Inhibitors of Proteasome Activity, Biochemistry, 42:8663-8670.
Gao, 2008, Design and Characterization of a Multisource Hand-Held Tandem Mass Spectrometer, Anal. Chem., 80:7198-7205.
Gao, 2006, Handheld Rectilinear Ion Trap Mass Spectrometer, Anal. Chem, 78:5994-6002.
Xu, 2010, Miniaturization of Mass Spectrometry Analysis Systems,, JALA, 15:433-439.
He, 2005, Arg9-peptide facilitates the internalization of an anti-CEA immunotoxin and potentiates its specific cytotoxicity to target cells, Int J. Biochem. Cell Biol., 37:192-205.
Heinzle, 1990, On-line fermentation gas analysis: error analysis and application of mass spectrometry, Analytica Chimica Acta, 238:101-115.
Hou, 2011, Sampling Wand for an Ion Trap Mass Spectrometer, Anal. Chem, 83:1857-1861.
Huang, 2011, Synchronized Inductive Desorption Electrospray Ionization Mass Spectrometry, Angew. Chem.-Int. Edit., 50:2503-2506.
Huang, 2011, Induced Nanoelectrospray Ionization for Matrix-Tolerant and High-Throughput Mass Spectrometry, Angew. Chem.-Int. Edit., 50:9907-9910.
Kato, 2011, Synthesis and pharmacological characterization of potent, selective, and orally bioavailable isoindoline class dipeptidyl peptidase IV inhibitors, Organic and Medicinal Chemistry Letters, 1:7.
Katritzky, 2008, Efficient Synthesis of Peptides by Extension at the N- and C-Terminii of Arginine, Org. Chem., 73:7153-7158.
Kim, 2003, Basic peptide system for efficient delivery of foreign genes, Biochem. Biophys. Acta, 1640:129-136.
Gao, 2009, Characterization of a discontinuous atmospheric pressure interface. Multiple ion introduction pulses for improved performance, International Journal of Mass Spectrometry, 283:30-34.
Li, 2014, Mini 12, Miniature Mass Spectrometer for Clinical and Other Applications—Introduction and Characterization, Anal. Chem., 86:2909-2916.
Mulligan, 2006, Desorption electrospray ionization with a portable mass spectrometer: in situ analysis of ambient surfaces, Chem. Com., 709-1711.
Narayanan, 2014, Molecular Ionization from Caron Nanotube Paper, Angew. Chem. Int. Ed., 53: 5936-5940.
Ouyang, 2009, Miniature Mass Spectrometers, Ann. Rev. Anal. Chem., 2:187-214.
Sanders, 2009, Hand-held Mass Spectrometer for Environmentally Relevant Analytes Using a Variety of Sampling and Ionization Methods, Euro. J. Mass Spectrom., 16:11-20.
Sokol et al., 2011, Miniature mass spectrometer equipped with electrospray and desorption electrospray ionization for direct analysis of organics from solids and solutions, Int. J. Mass Spectrum. 306:187-195.
Turhan, 2011, In situ IR monitoring of complexation reaction between 2,6-bis(3,5-dimethylpyrozoyl) pyridine and some metal ions, Vibrational Spectroscopy, 56:111-115.
Varani, 1997, RNA-Protein Intermolecular Recognition, Acc. Chem. Res., 30:189-195.
Wang, 2006, Arginine-rich intracellular deliverty peptides noncovalently transport protein into living cells, J. Biochemical and Biophysical Research Communications, 346:758-767.

* cited by examiner

REACTION MONITORING

RELATED APPLICATIONS

This application claims priority to and benefit of U.S. Provisional Patent Application Ser. No. 62/375,927, filed Aug. 17, 2016, U.S. Provisional Patent Application Ser. No. 62/374,146, filed, Aug. 12, 2016, and U.S. Provisional Patent Application Ser. No. 62/372,505, filed Aug. 9, 2016. The contents of each of the above applications are incorporated by reference herein in their entireties.

FIELD OF THE INVENTION

The invention generally relates to systems and methods for on-line reaction monitoring.

BACKGROUND

Control of reacting mixtures is important in chemical, pharmaceutical and other manufacturing processes and is best achieved by knowledge of the concentrations of all chemical species present over the course of the reaction. Process analytical technology (PAT) methodology as endorsed by the U.S. Food and Drug Administration (FDA) is a system for designing, analyzing, and controlling manufacturing through timely measurements (i.e., during processing) of critical quality and performance attributes of raw and in-process materials and processes, with the goal of ensuring final product quality. PAT has been widely applied in pharmaceutical development, scale-up, and manufacture. In the FDA's PAT definition "analyzing" equates to in situ analytical tools.

An on-line reaction monitoring system based on inductive-ESI-MS (iESI-MS) has been reported as a simple way to monitor chemical reactions in real time. See X. Yan, E. Sokol, X. Li, G. T. Li, S. Q. Xu, R. G. Cooks, Angew. Chem.-Int. Edit. 2014, 53, 5931-5935, incorporated herein by reference.

Besides the qualitative analysis of species in the reaction mixture, quantitative information on the starting materials, intermediates and products is needed and achieving this capability is much more demanding. Detailed reaction kinetics can be obtained only when quantitative monitoring tools are available. Unfortunately, in the available reaction monitoring systems, ion current intensities in mass spectrometry alone do not always correlate precisely, accurately, or directly with the amount of compound present in the sample. This is due to differences in ionization efficiencies and is true regardless of the ionization technique or instrument employed. Adding to the difficulty of this measurement is the fact that reactant, intermediate and product concentrations will vary greatly over the course of a synthesis, with the working concentrations of particular analytes often falling outside of the linear dynamic range. Therefore, there are no generally applicable mass spectrometry methods for on-line quantitation of analytes in reacting solutions.

SUMMARY

The invention provides systems and methods for quantitative on-line reaction monitoring. Aspects of the invention are accomplished with a quantitation unit that is configured to introduce an internal standard and optionally one or more dilution solvents into a portion of a reaction solution flowed from a reaction vessel. In that manner, continuous on-line quantitative reaction monitoring is achieved. The advance represented by iESI-MS described above opens up the opportunity of on-line MS as a PAT tool in quantitative reaction monitoring. The present invention identifies and addresses certain obstacles in MS-based and other PAT on-line reaction monitoring tools such as the requirement that to achieve on-line MS quantitation, an internal standard (IS) needs to be introduced into the reaction mixture and selected so that it will not complicate the reaction or the later product separation so that its concentration is appropriate (or appropriately adjusted) to cover the range of the analyte(s).

Systems and methods of the invention further provide for on-line monitoring of long reactions (e.g., greater than 1 hour) without sample carryover and with high quality signals. Through multiple reaction monitoring, data collection time for long reactions can be compressed and reactions may be run in parallel to improve laboratory efficiency and sample processing throughput.

In certain embodiments, the invention provides systems that include a reaction vessel having an outlet, a quantitation unit coupled to the outlet and configured to introduce internal standard and solvent into reaction solution flowed from the reaction vessel, one or more ion generating devices that receive flow from the quantitation unit, and a mass spectrometer.

There are numerous possible configurations for the quantitation unit and the skilled artisan will appreciate that the specific configuration will depend on the reaction being monitored and the dilution factor needed for reaction monitoring. In certain embodiments, the quantitation unit includes one or more junctions (e.g., one, or a plurality of junctions) that allow for introduction of the internal standard and the solvent into the reaction solution. In some embodiments, only a single junction is used to introduce an internal standard. In other embodiments, a plurality of junctions are used. In such embodiments, for example, a first junction is connected to an internal standard reservoir. The quantitation unit may then include second, third, and fourth junctions, one or more of which are connected to one or more solvent reservoirs. The quantitation unit may include a fifth junction coupled to a waste reservoir.

The systems of the invention may include one or more ion generating devices. The number of ion generating devices will depend on the configuration of the quantitation unit and the number of different dilutions to be measured for quantification. For example, in an embodiment using seven junctions, there are typically two outlets from the quantitation unit. In such an embodiment, the system would include two ion generating devices. As discussed herein, there are certain advantages to using inductive charging for each ionization device, although this is not required and other ionization techniques can be used. In certain embodiments though, each ion generating device is configured for inductive charging electrospray ionization. In certain embodiments, the quantitation unit may include tubing having different internal diameters.

Other aspects of the invention provide methods for quantifying a reaction in real-time that involve conducting a reaction in a first solvent in a vessel. A portion of reaction solution is then flowed out of the vessel and through a main channel. An internal standard and first dilution solvent are introduced into the reaction solution that are flowing through the main channel to produce a mixture of the diluted reaction solution and the internal standard. In order to reach a uniform mixture and avoid backpressure, the solution flows through a 7-way mixer, a 5-way mixer and a union. Then the solution flows to an ion generating device. Ions of one or more analytes in the reaction solution and ions of the internal standard are generated with the ion generating device. The ions are then analyzed, thereby monitoring the reaction in real-time.

In certain embodiments, after the introducing and first dilution steps, methods of the invention may additionally involve splitting at one or more junctions with the main channel, the mixture of the reaction solution and the internal standard from the main channel into one or more secondary channels. In certain embodiments, the junctions are arranged sequentially. The methods may then further involve introducing a second solvent (same or different from the first solvent) to the mixture of the reaction solution and the internal standard at one or more junctions. The second solvent may be used to dissolve a precipitation to avoid fouling the system. The one or more of the secondary channels may be each coupled to an ion generating device. In certain embodiments, the flowed portion of the first solvent from the reaction vessel acts as the ionization solvent. In certain embodiments, the flowing, introducing, and generating step are continuous.

In certain aspects, the invention provides systems for multiple reaction monitoring that include a plurality of reaction vessels, a plurality of ion generating devices, a plurality of channels (e.g., fused silica capillaries), each channel coupling a reaction vessel to an ion generating device, an actuator coupled to the plurality of ion generating devices to thereby allow movement of the plurality of ion generating devices, and a mass spectrometer. In certain embodiments, the plurality of ion generating devices may be nano-electrospray ionization probes. In some embodiments, the system can be configured for inductive charging of each of the plurality of ion generating devices individually.

The actuator may include a rotary stage that holds the plurality of ion generating devices. The actuator may also include an electrode positioned proximate the rotary stage to impart an electric charge to each of the plurality of ion generating devices as each of the plurality of ion generating devices rotate past the electrode.

In certain embodiments, the one or more of the plurality of reaction vessels may be pressurized. The system may further include a discontinuous atmospheric pressure interface, such as described in U.S. Pat. No. 8,304,718, the content of which is incorporated by reference herein in its entirety. The system may also include one or more heating elements associated with one or more of the plurality of reaction vessels.

In other aspects, the invention provides methods for multiple reaction monitoring that include conducting a plurality of reactions simultaneously in a plurality of reaction vessels, simultaneously flowing a reaction solution from each of the plurality of reaction vessels to a plurality of ion generating devices coupled to an actuator that comprises an electrode, sequentially generating ions of each reaction solution from each of the plurality of ion generating devices as each ion of the plurality of ion generating devices is moved into proximity of the electrode of the actuator, and sequentially analyzing the ions of each reaction solution. Analyzing may involve sequentially introducing the ions of each reaction solution into a mass spectrometer (bench-top or miniature). In certain embodiments, the ions of each reaction solution are discontinuously introduced into the mass spectrometer through use of a discontinuous atmospheric pressure interface. In certain embodiments, the at least one of the plurality of reaction vessels is heating during the conducting step.

The mass spectrometer used in the system and methods described herein may be, for example, any bench-top mass spectrometer or miniature mass spectrometer.

BRIEF DESCRIPTION OF THE DRAWINGS

FIG. 4A is an on-line quantitation calibration curve of L-Arg. FIG. 4B is an on-line quantitation calibration curve of Cbz-L-Val-L-Arg. Samples were collected at O1 and O2 using Arg-$^{13}C_6$ as internal standard in both.

FIG. 5A shows flow directions and FIG. 5B shows a selected ion chronogram of $[L-Arg-H]^+$.

(FIG. 6B) after purification; (FIG. 6C) after acidifying and (FIG. 6D) after sodiating. Note the different ratio of protonated/sodiated products.

(FIG. 7B) optimized reaction; (FIG. 7C) optimized conditions for reaction monitoring.

DETAILED DESCRIPTION

On-line continuous monitoring of solution phase reagent concentrations is difficult to achieve, unlike head space (vapor) analysis for which a large set of methods is possible including gas chromatography/high-performance liquid chromatography, IR spectroscopy, Ramen spectroscopy, nuclear magnetic resonance and electrochemistry.

The difficulties of on-line continuous solution-phase monitoring lie in both the sampling step and in the measurement step. The former must be achieved without significantly depleting the bulk sample in the reactor and without phase change during transfer. The measurement step is complicated by the fact that reactant, intermediate and product concentrations vary greatly over the course of a reaction, that working concentrations of particular analytes often lie outside of the linear dynamic range for particular measurement devices, the fact that very rapid measurements are needed, and the fact that complex mixtures must be analyzed. Several process analytical chemistry (PAC) tools have been utilized to address this problem, and among them IR and Raman spectroscopy are prominent.

The capabilities of mass spectrometry for trace as well as bulk analysis, as well as the molecular specificity and speed of the technique make it highly attractive for application in on-line reaction monitoring. Amongst the ionization methods that are available for solution phase analysis, spray based methods like ESI are the most attractive but the propensity for the tips in ESI and especially nESI emitters to clog is a severe drawback. The use of porous media for paper spray and related ionization methods addresses this problem but continuous, long-term quantitative analysis using PS has not been demonstrated.

One solution to the problem is inductive application of the voltage needed to create charged droplets. Inductive electrospray ionization (iESI) is a variant of electrospray ionization (ESI) which accurately controls the creation of charged droplets by placing an electrode near a spray emitter and pulsing it repetitively to high positive potential. Inductive ESI provides several new capabilities: it is characterized by a remarkable tolerance to matrix and to salt effects and it has a high efficiency. iESI avoids the clogging problem because the DC voltage pulse circuit 'rings' by polarizing the solution first in one direction then in the opposite and avoiding product build up from electrochemical reactions and/or solvent evaporation at the spray tip. Inductive electrospray ionization is described for example in U.S. Pat. No. 9,184,036 and U.S. patent application publication number 2014/0051180, the content of each of which is incorporated by reference herein in its entirety.

Figure 1:
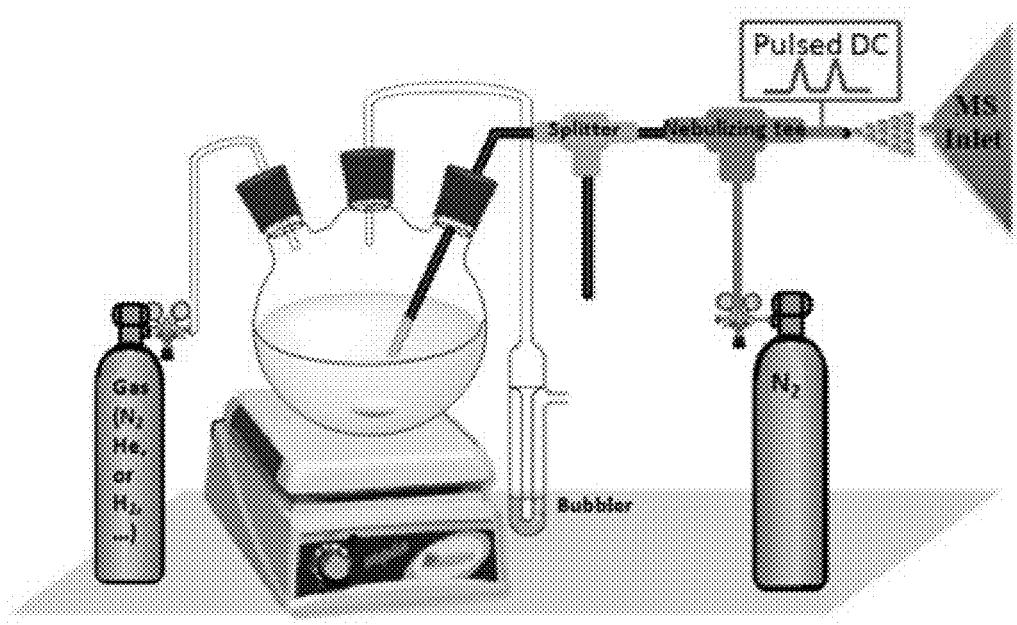
FIG. 1 is a diagram of a prior art inductive ESI-MS on-line reaction monitoring system.

An on-line reaction monitoring system based on inductive-ESI-MS (iESI-MS) has been reported as a simple way to monitor chemical reactions in real time. Such a system is described in U.S. patent application publication number 2014/0051180, the content of which is incorporated by reference herein in its entirety. This system automatically samples reaction mixtures in-situ, delivers them to the MS inlet, continuously monitors the reaction mixture and so provides virtually real-time information on the nature of intermediates and products in the mixture by observing their dynamic profiles as shown in FIG. 1. This method has the signal advantage of being applicable to concentrated solutions of the type encountered in pharmaceutical manufacturing without emitter clogging problem. Moreover, this monitoring system avoids sample pre-treatment and chromatography while maintaining the integrity of the analytes and reducing the analysis time for each reaction.

As discussed above, besides the qualitative analysis of species in the reaction mixture, quantitative information on the starting materials, intermediates and products is needed and achieving this capability is much more demanding. Detailed reaction kinetics can be obtained only when quantitative monitoring tools are available. Unfortunately, in the available reaction monitoring systems (including that of FIG. 1), ion current intensities in mass spectrometry alone do not always correlate precisely, accurately, or directly with the amount of compound present in the sample. This is due to differences in ionization efficiencies and is true regardless of the ionization technique or instrument employed.

Figure 2A:
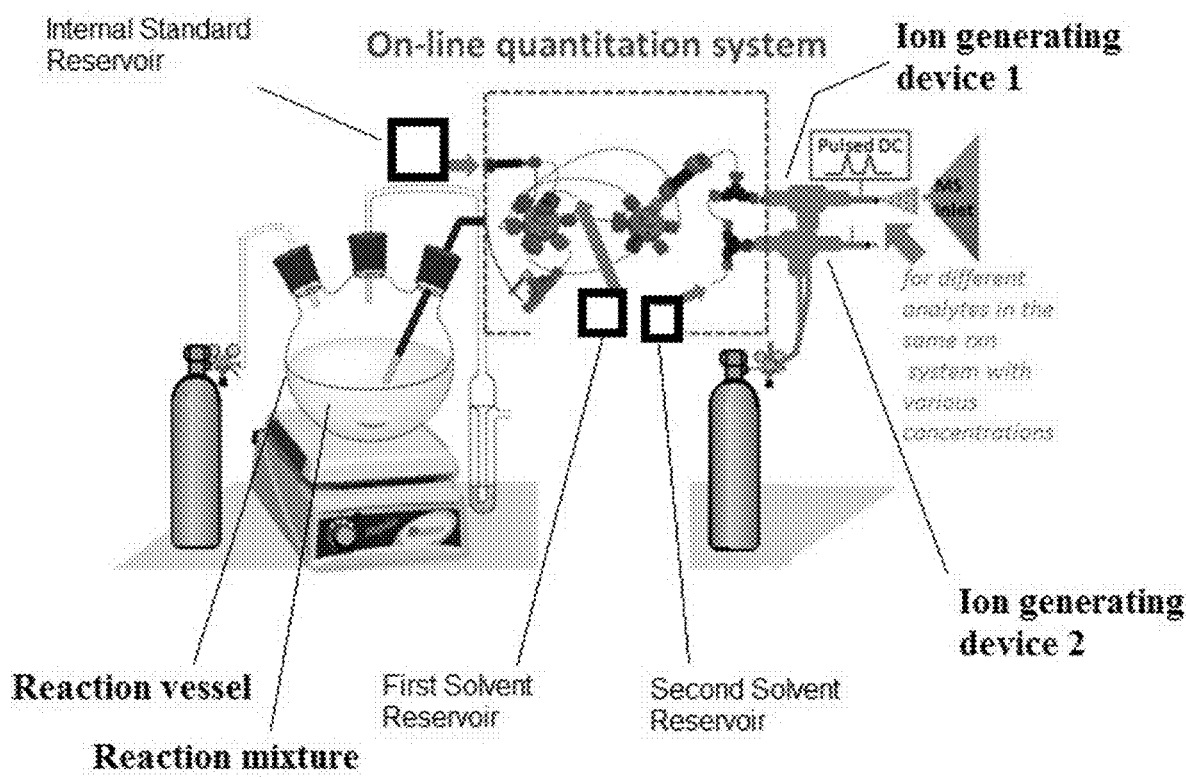
FIG. 2A shows an on-line reaction monitoring quantitation system of the invention.
Figure 2B:
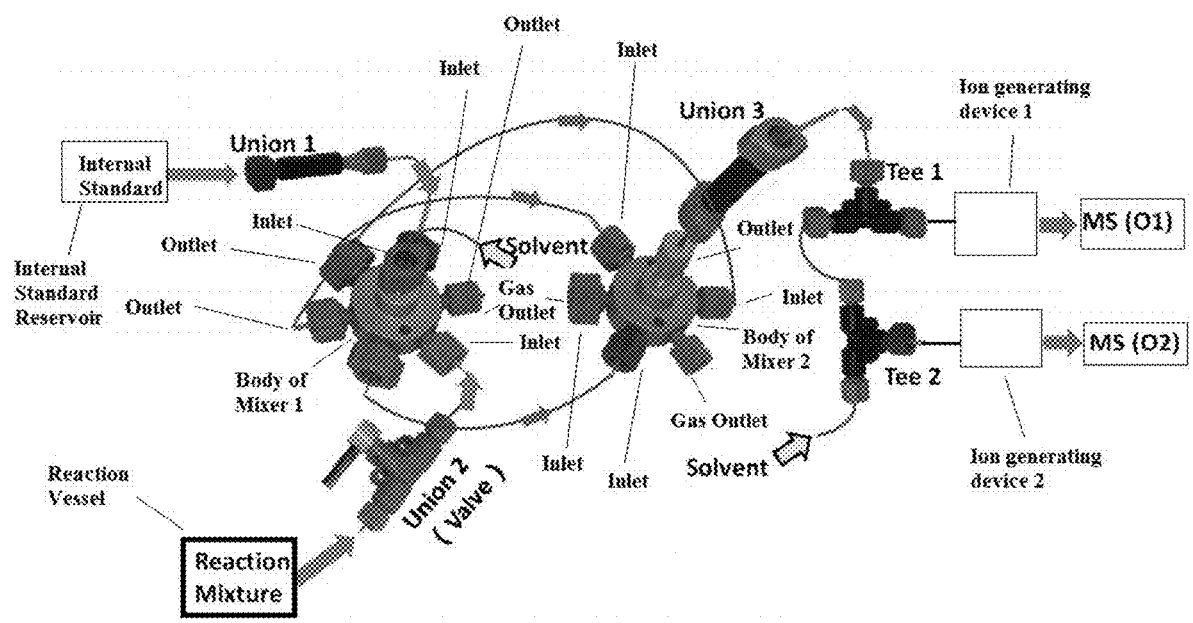
FIG. 2B is an exemplary illustration of flow directions and mixers in the plug-in quantitation device shown in FIG. 2A.

The invention provides an on-line device based on iESI-MS to determine the concentrations of compounds of interest in reaction mixtures (FIGS. 2A-B). The reaction solution in the sealed reaction vessel is transferred under positive gas pressure through the plug-in quantitation unit via a capillary to a selected emitter-spray tip, where a positive potential is pulsed repeatedly to produce transient strong electric fields in the spray solution. These voltage pulses result in emission of bursts of charged droplets. The potential is provided by a home-built power supply with the output of 860 V at 2000 Hz. Sheath gas can be used to aid in the nebulization process, to minimize variations in droplet size and to protect the nebulized reaction mixture from the surrounding atmosphere. Without wishing to be tied to a particular theory, it is believed that capillary blockages in such a device may be avoided even after operating for long periods with concentrated reaction solutions due potentially to a self-cleaning feature associated with the rapid forward and reverse potentials experienced in the solution during to ringing of the inductive circuit.

In this exemplary embodiment, the plug-in quantitation device (FIG. 2B) is composed of seven junctions: union 1 being used for introducing the internal standard, union 2 as a valve to control the introduction of reaction solution, mixer 1, 2 and union 3 for mixing of internal standard, here formic acid (to remove sodiated product ion, to be discussed later) into the reaction solution and spray solvent, tee 1 is used to split the working solution to the MS inlet and tee 2 for further dilution with spray solvent. The skilled artisan will appreciate that this embodiment is only exemplary and that numerous different designs, using a different number of junctions is within the scope of the invention and only depends on the number of dilutions desired to be analyzed.

Valves of the device may be any valve capable of selectively allowing or stopping flow of a liquid within tubing or channels of the invention. For example ball valves, butterfly valves, gate valves, globe valves, needle valves, or other valves known in the art may be used.

Turning back to the exemplary embodiment, as the reaction mixture, internal standard and large flow of spray solvent converge at mixer 1, the increased pressure is released by four outlets of mixer 1 and converge again in mixer 2 with outlet capillary of larger ID (e.g., 530 µm). The design also disrupts the laminal flow and greatly enhances the mixing of three different compounds. Union 3 helps further mixing and completes in a uniform solution. In this device, two outlets (O1 and O2) are provided, each subjecting the reaction mixture to a different dilution factor, and each connected to a separate iESI emitter to provide on-line quantitation of analytes present over particular ranges of concentrations.

In certain embodiments, systems and methods of the invention relate to on-line multiple reaction monitoring. In various embodiments, on-line reaction monitoring may be carried out by slightly pressurizing a reaction vessel using air or an inert gas. The solution can then be flowed through a fused silica filling a continuous-flow nano-electrospray (CF-nESI) emitter. The solution may then be analyzed with a mass spectrometer (e.g., a home-built miniature mass spectrometer such as the Mini 12 described in Li, et al., Mini 12, Miniature Mass Spectrometer for Clinical and Other Applications—Introduction and Characterization, Anal. Chem., 2014, 86 (6), pp 2909-2916, incorporated herein by reference). Multi-sample monitoring can be performed in a similar manner but with multiple pressurized reaction vessels delivering solution to multiple CF-nESI emitters. As the instrument is running, the CF-nESI probes may be moved in front of the MS inlet using an automated linear actuator and analyzed sequentially for several hours until the reaction is complete. Reactions can be analyzed for several hours with a time resolution of, for example, 20 seconds allowing four reactions to be monitored simultaneously with a time resolution 80 seconds.

Figure 10:
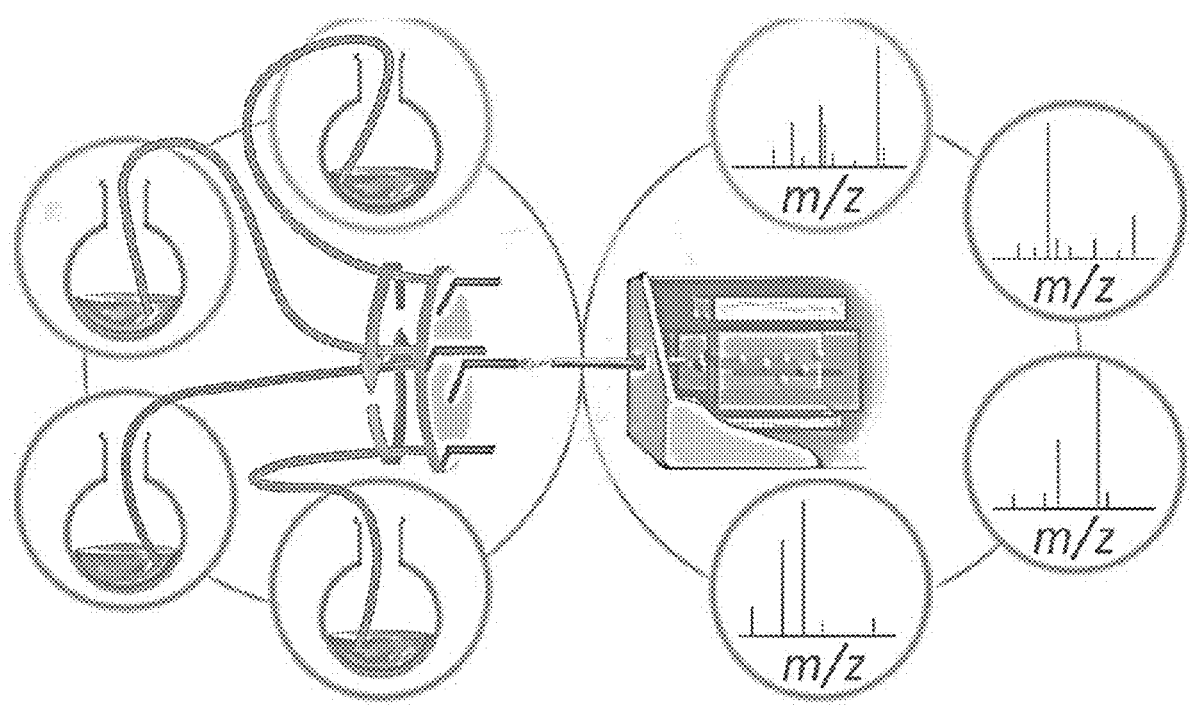
FIG. 10 is an illustration of an exemplary multiple reaction monitoring system.

An exemplary system of the invention is shown in FIG. 10. The system includes a plurality of reaction vessels. In this exemplary system, four reaction vessels are shown, but the skilled artisan will appreciate that the systems of the invention can include more or fewer vessels, depending on the number of reactions to be monitored. The illustrated embodiment shows unpressurized vessels. However, in certain embodiments, pressurized reaction vessels are used. In such embodiments, the reaction vessel includes a port such that gas can be introduced into the vessel and a second outlet port. While not shown in FIG. 10, one or more heating elements can be used with any number of the reaction vessels.

Each vessel can include a channel or tube that extends from the vessel to an actuator. The channel or tube allows a portion of reaction solution in each vessel to flow out of each reaction vessel as the reactions are occurring in the vessels. Exemplary channels include, for example, fused silica capillaries but the invention is not limited to only fused silica capillaries. Any tubing can be used and the choice will be based on the reaction to be monitored (e.g., to minimize chemical interaction with the tubing/channel), desired flow rate, etc. The channel can be clear, opaque, translucent, etc., depending on the light sensitivity of the reaction and to allow for observation of the system. The reaction vessels as well as the mixers, valves, and other components described herein may be constructed of similar materials based on the same considerations as given for the channel materials.

The channels may then each couple to an actuator, which is exemplarily shown in FIG. 10 as a rotating circular stage. The actuator can include a plurality of ion generating devices, one for each channel. A motor may drive rotation of the stage such that each ion generating device sequentially aligns with an inlet of the mass spectrometer shown in FIG. 10. Upon alignment, the aligned ion generating device can be triggered to generate a spray discharge that causes the reaction solution to be ionized. The generated ions can then be transmitted into the mass spectrometer for analysis. The system may be configured such that only the aligned ion generating device generates a spray discharge while the other ion generating devices on the stage do not produce a spray discharge until aligned with the inlet of the mass spectrometer. Actuators may be sequential as described below with respect to FIGS. 13 and 14 or may be operable to align ion generating devices with the mass spectrometer inlet and generate spray in any order. In certain embodiments, the actuator (e.g., a rotating circular stage) may be computer controlled and indexed in order to allow the computer to identify a particular reaction vessel to sample, position the associated ion generating device in alignment with the MS inlet, and cause the ion generating device to generate a spray discharge into the inlet. The actuator may be indexed for visual identification of ion generating devices (e.g., via barcodes and optical sensors in communication with the computer) or physically indexed (e.g., via notches or a toothed gear for precise rotation and positional memory in a circular stage).

Any mass spectrometer known in the art can be used with systems and methods of the invention. The mass spectrometer may be a bench-top mass spectrometer or a miniature mass spectrometer, such as described for example in Gao et al. (Z. Anal. 15 Chem. 2006, 78, 5994-6002), Gao et al. (Anal. Chem., 80:7198-7205, 2008), Hou et al. (Anal. Chem., 83:1857-1861, 2011), Sokol et al. (Int. J. Mass Spectrom., 2011, 306, 187-195), Xu et al. (JALA, 2010, 15, 433-439); Ouyang et al. (Anal. Chem., 2009, 81, 2421-2425); Ouyang et al. (Ann. Rev. Anal. Chem., 2009, 2, 187-25214); Sanders et al. (Euro. J. Mass Spectrom., 2009, 16, 11-20); Gao et al. (Anal. Chem., 2006, 78(17), 5994-6002); Mulligan et al. (Chem. Com., 2006, 1709-1711); and Fico et al. (Anal. Chem., 2007, 79, 8076-8082), the content of each of which is incorporated herein by reference in its entirety.

Figure 11:
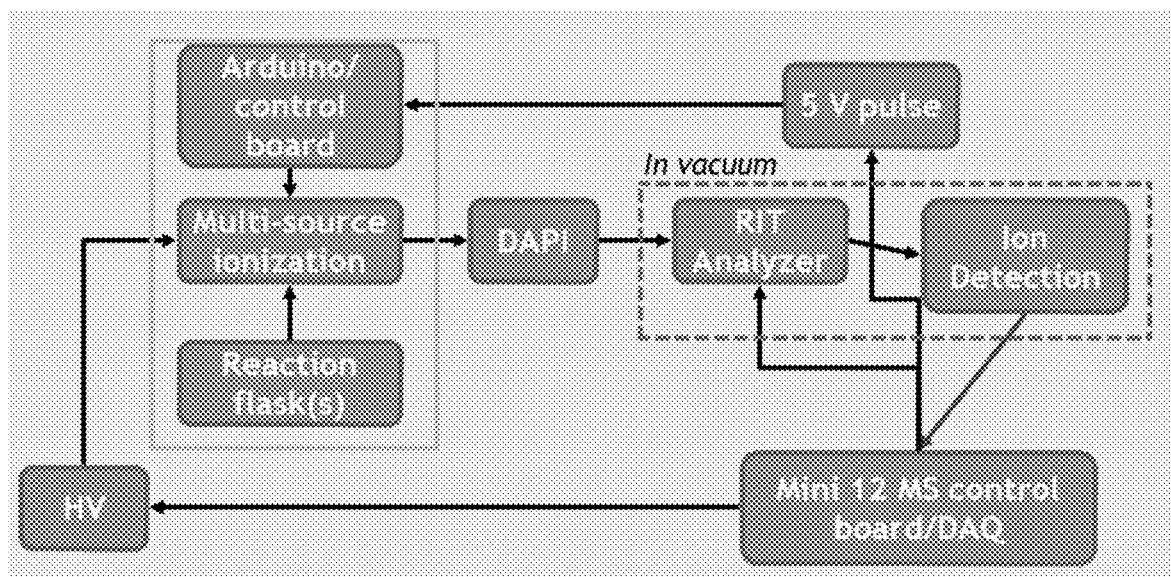
FIG. 11 is an illustration of a system diagram.
Figure 12:
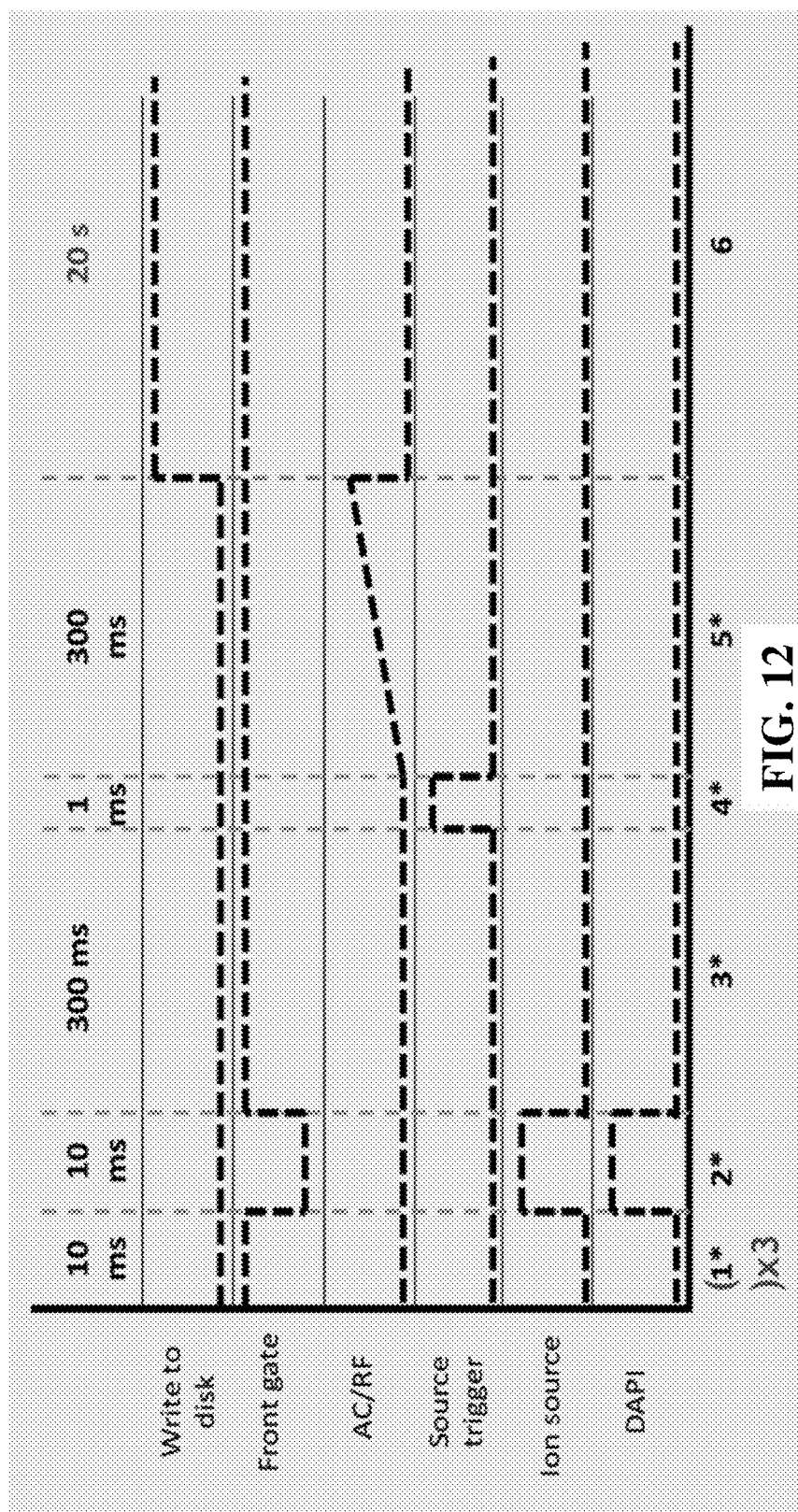
FIG. 12 shows a scan table for continuous monitoring.

FIG. 11 is a diagram of certain systems according to the invention. As shown in FIG. 11, the control circuitry of the mass spectrometer (miniature mass spectrometer in the illustrated case) is coupled to control circuitry for the actuator so that ion generation can be synchronized with the mass analysis. FIG. 12 illustrates a scan table for continuous monitoring that can be accomplished using an inductive charging electrospray ionization configuration for the ion generating device. Inductive charging electrospray ionization and exemplary configurations of systems for such are described herein and for example in U.S. Pat. No. 9,184,036 and U.S. patent application publication number 2014/0051180, the content of each of which is incorporated by reference herein in its entirety.

Figure 13:
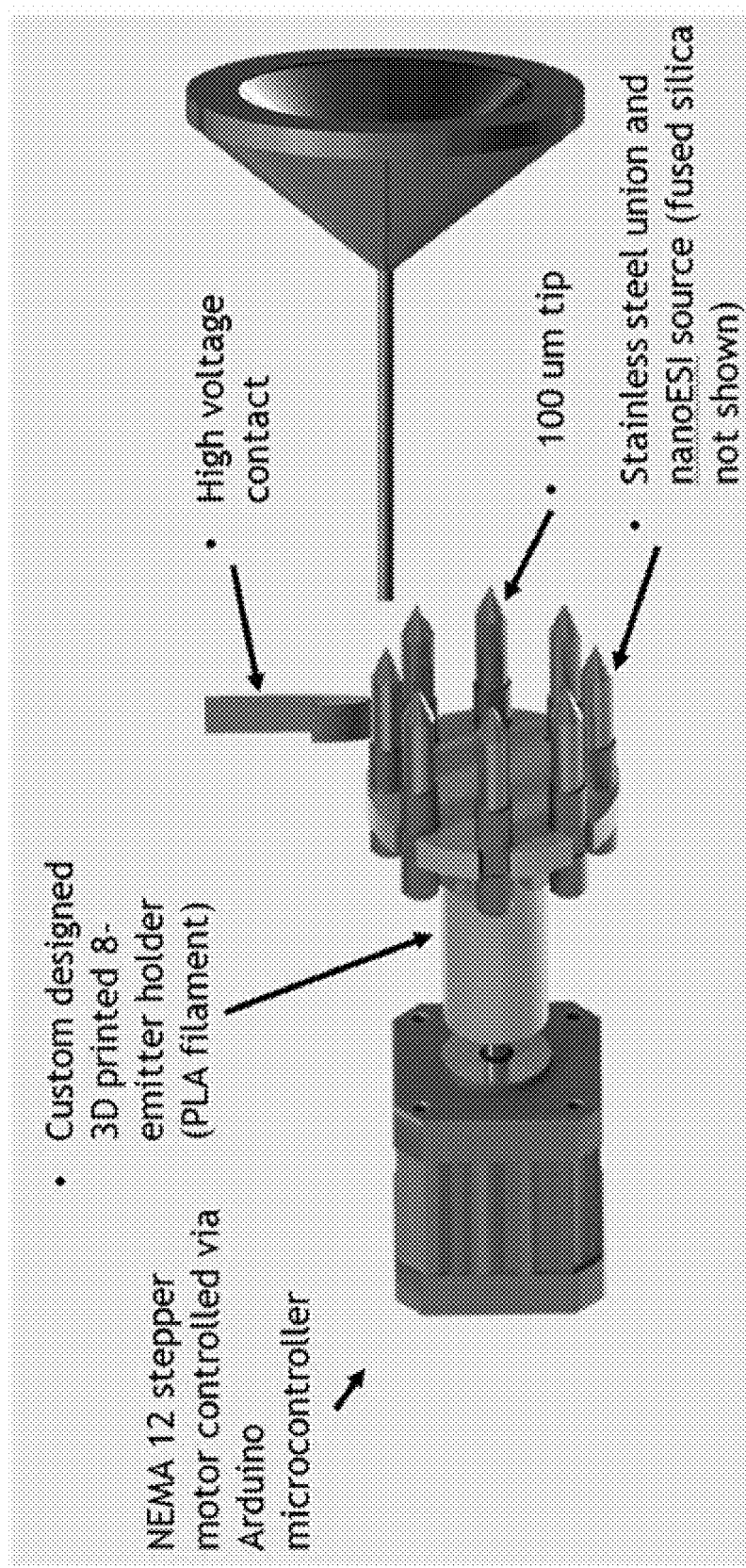
FIG. 13 is an illustration of an exemplary actuator with ion generating devices configured for inductive charging electrospray ionization.
Figure 14:
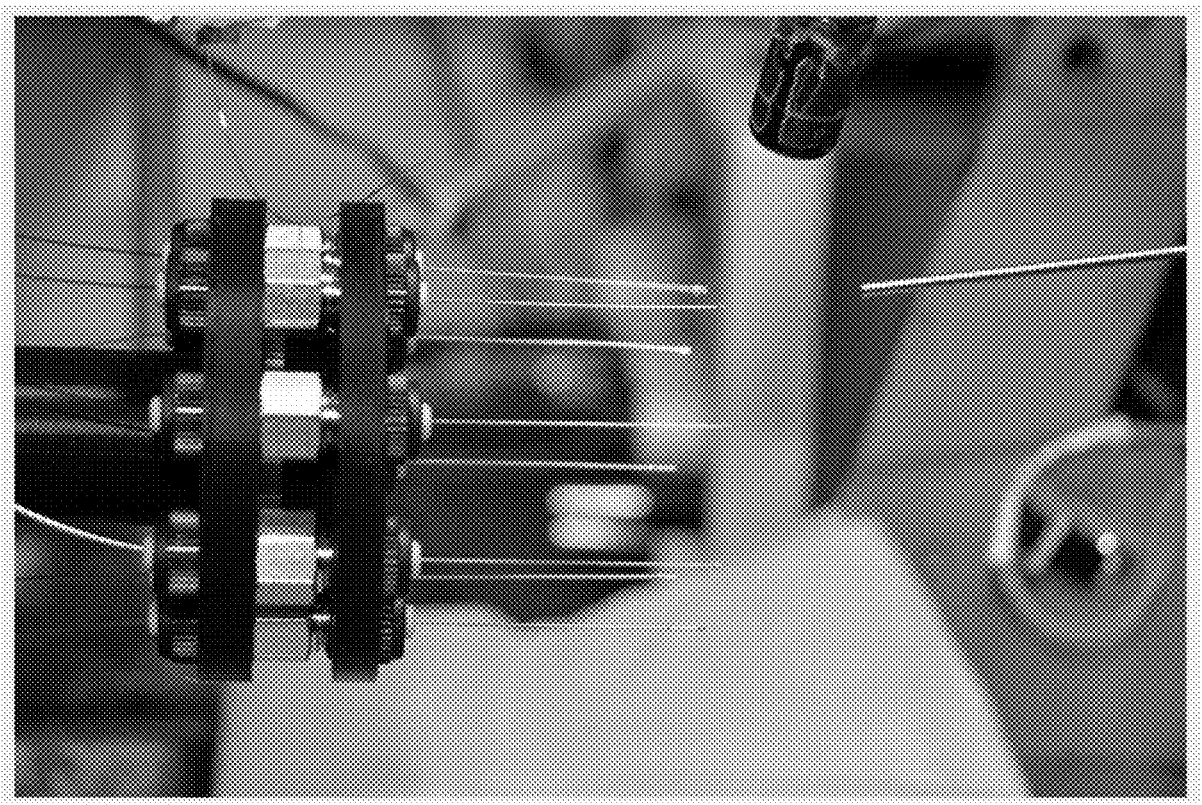
FIG. 14 is a photograph of an exemplary actuator as illustrated in FIG. 13.

FIGS. 13-14 illustrate an exemplary actuator with ion generating devices, in which the system is configured for inductive charging. As shown in FIGS. 13-14, the circular stage is coupled to a motor that drives rotation of the stage. The stage includes eight ion generating devices and the skilled artisan will appreciate that this is systems featuring more or less ion generating devices are contemplated by the present invention. Each channel couples to each ion generating device. An electrode is then positioned in proximity to the stage. The stage is positioned so that the ion generating devices sequentially align with the inlet of the mass spectrometer during rotation of the stage as shown in FIGS. 13-14. In operation, the stage rotates, sequentially bringing each ion generating device into proximity with the electrode while its outlet aligns with the inlet of the mass spectrometer so that an electric discharge from the electrode can be inductively imparted to the reaction solution in the ion generating device that is proximate the electrode. The other ion generating devices are unaffected by the locally produced electric discharge. In that manner, electric discharge is only imparted to the proximate ion generating device, and only that ion generating device produces a spray discharge that enters the inlet of the mass spectrometer. The stage then rotates to the next ion generating device.

Using such a set-up, reaction solution from multiple reactions can be sequentially and continuously injected into the mass spectrometer for analysis. In that manner, multiple reactions may be simultaneously monitored over a period of time.

Turning back to FIG. 11, systems and methods of the invention can be carried out with a discontinuous atmospheric pressure interface, which is particularly useful when the mass spectrometer is a miniature mass spectrometer. A discontinuous atmospheric pressure interface, such as described in U.S. Pat. No. 8,304,718, the content of which is incorporated by reference herein in its entirety.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1

Figure 3:
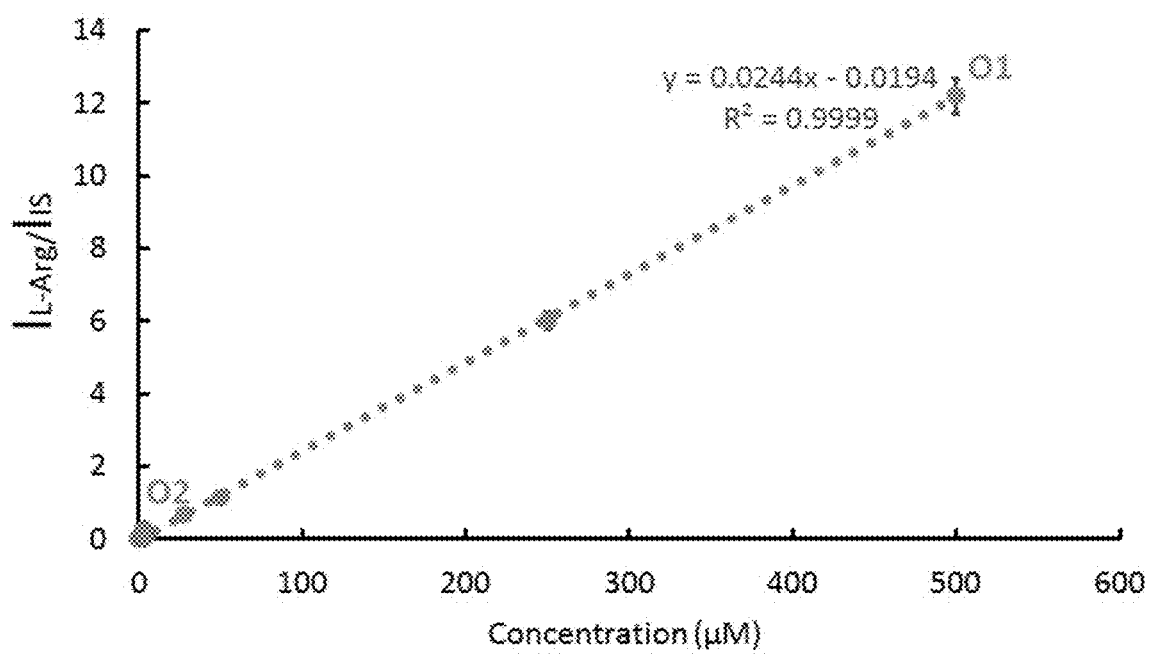
FIG. 3 is an off-line calibration curve of L-Arg using L-Arg-$^{13}C_6$ as internal standard. Red dots represent samples collected from two outlets.

A solution of L-Arg (100 μM) was prepared in ACN: $H_2O$ (v:v=2:1), injected at E1 (see FIG. 2B) and mixed with an equal amount of solvent (ACN: $H_2O$, v:v=2:1) injected at E2. The same solvent was infused simultaneously at E3 and E4. Samples were collected from outlets 1, 2, (O1, O2, FIG. 2B), mixed with internal standard L-Arg-$^{13}C_6$ (50 μM) and analyzed by iESI-MS. Based on the off-line calibration curve recorded for L-Arg (FIG. 3), the concentrations of L-Arg after dilution were determined. With fixed capillary IDs, angles and positions of the tees, the dilution factor can be related to the pressure (hence flow rate) at E1-E4.

The device produced different dilution factors at each outlet, which allows compatibility of samples with different concentrations in one mixture using dilution factors that cause their concentrations to fall to within their linear dynamic ranges for each chosen sprayer (and hence dilution factor) and so optimize quantification by MS. The optimized conditions were found when using a flow rate of 30 μL/min for E1 and E2, 450 μL/min for E3 and E4, they corresponded to 17 times dilution at O1, 255 times dilution at O2 (shown by the labelled dots in FIGS. 4A-B). The experiment with optimized conditions was repeated five times and showed 8% variance. The variation between each batch could be reduced by fixing the configuration of the device. O2 has the higher dilution factor which makes it useful for quantitation of concentrated compounds (e.g. reagents at the beginning of a reaction and products at the end of a reaction), while O1 with the lower dilution factor meets the needs of quantitation of less concentrated compounds (products at the beginning and reagents at the end, and trace intermediates or impurities). Volumes were also measured for each sample and flow rates were calculated at each outlet.

System dead time can be defined as the lag between the status of the bulk-phase reaction and the time of subsequent mass analysis. L-Arg was injected into E1 (FIG. 5A), while solvent ($HCN:H_2O$, v:v=2:1) was added through E2, E3 and E4. The dead time was found to be 20 s at O1, and 30 s at O2, as evaluated by observing the time before the emergence of L-Arg in the full mass scan (shown in form of ion chronogram, FIG. 5B). The dead time suggests that after switching the emitters an approximately 30 second delay is required before collection of data for the next time point.

Figure 4A:
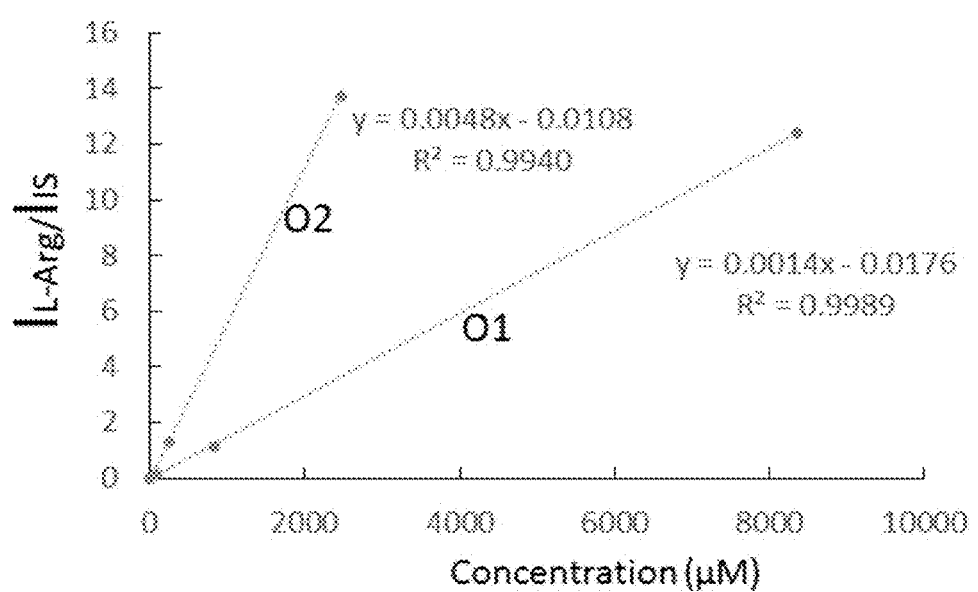
FIGS. 4A-B are on-line quantitation calibration curves.
Figure 4B:
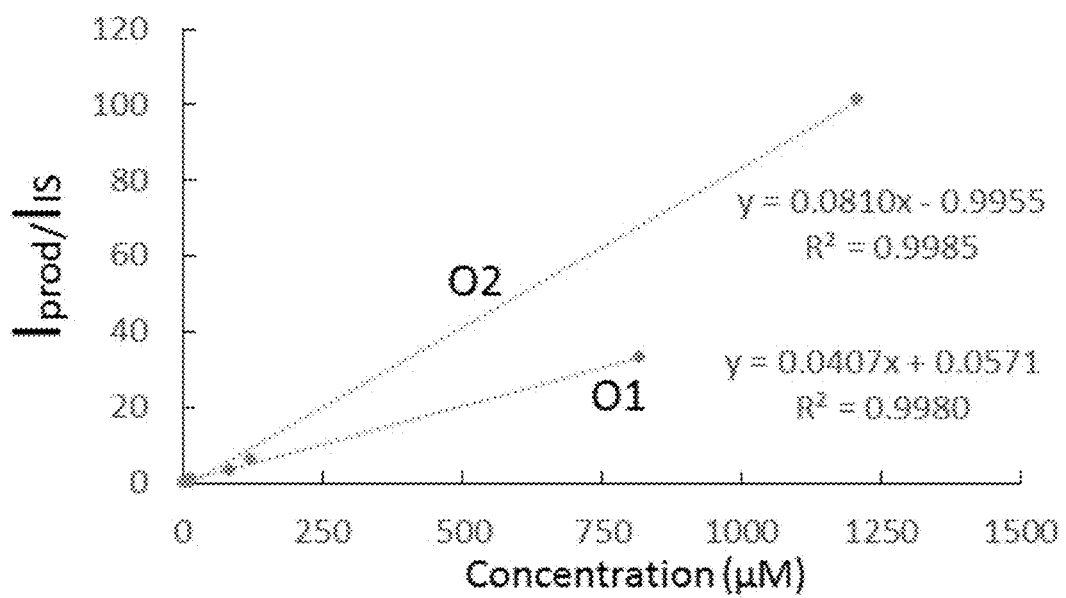
Figure 6A:
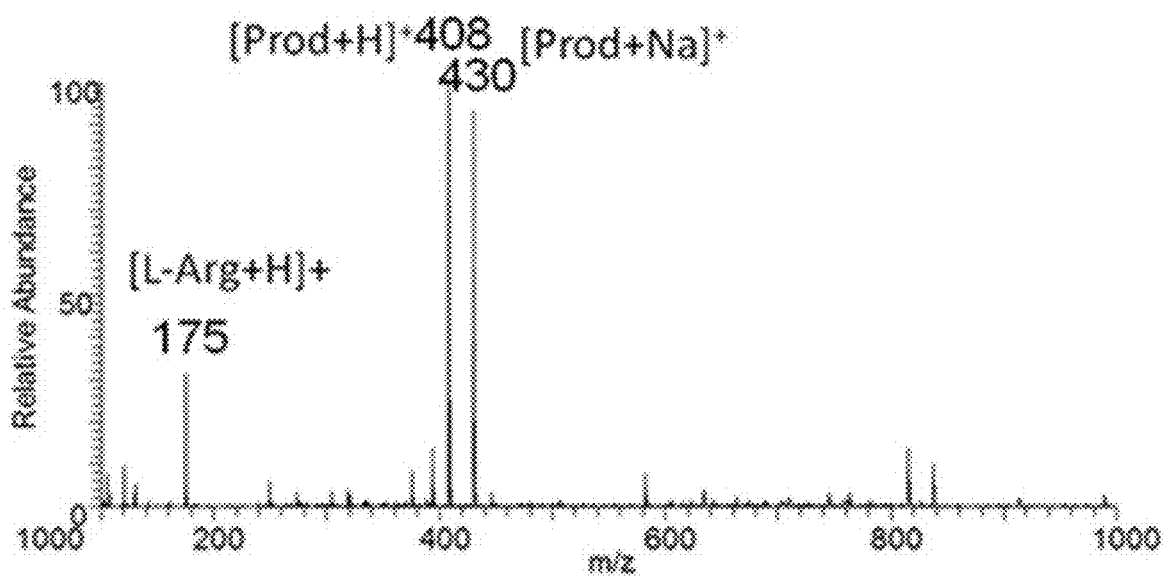
FIGS. 6A-D show mass spectra of product Cbz-L-Val-L-Arg taken (FIG. 6A) from in the reaction mixture.
Figure 6B:
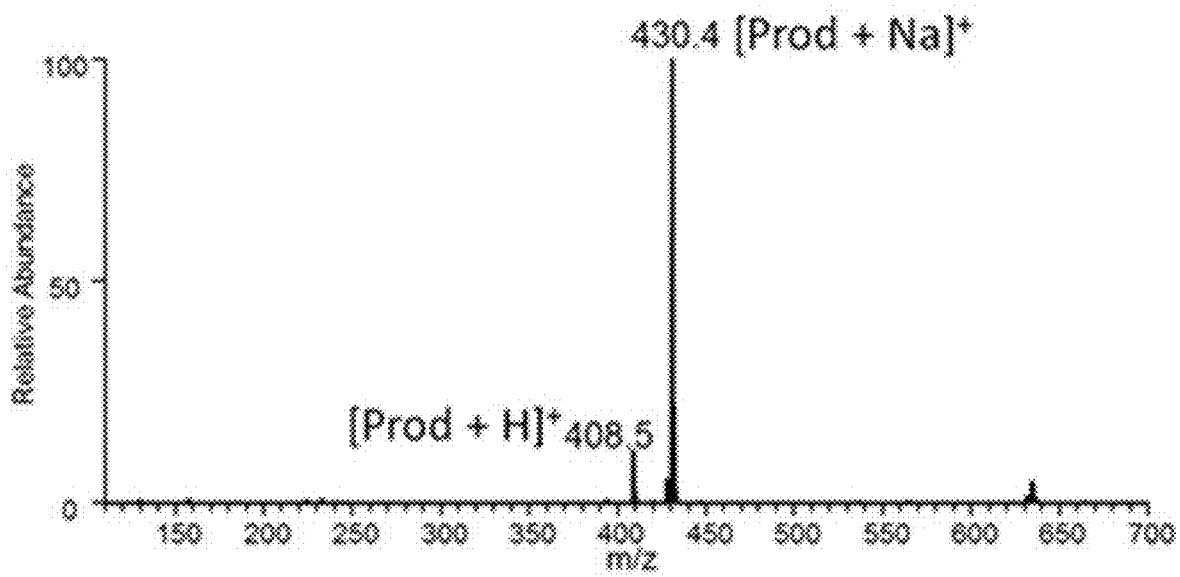
Figure 6C:
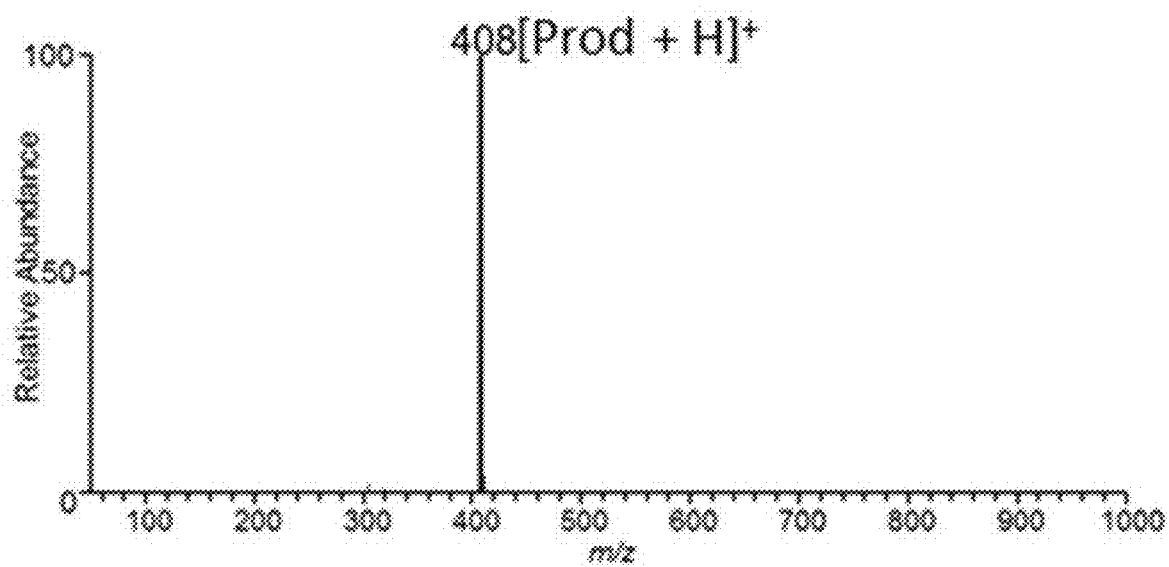
Figure 6D:
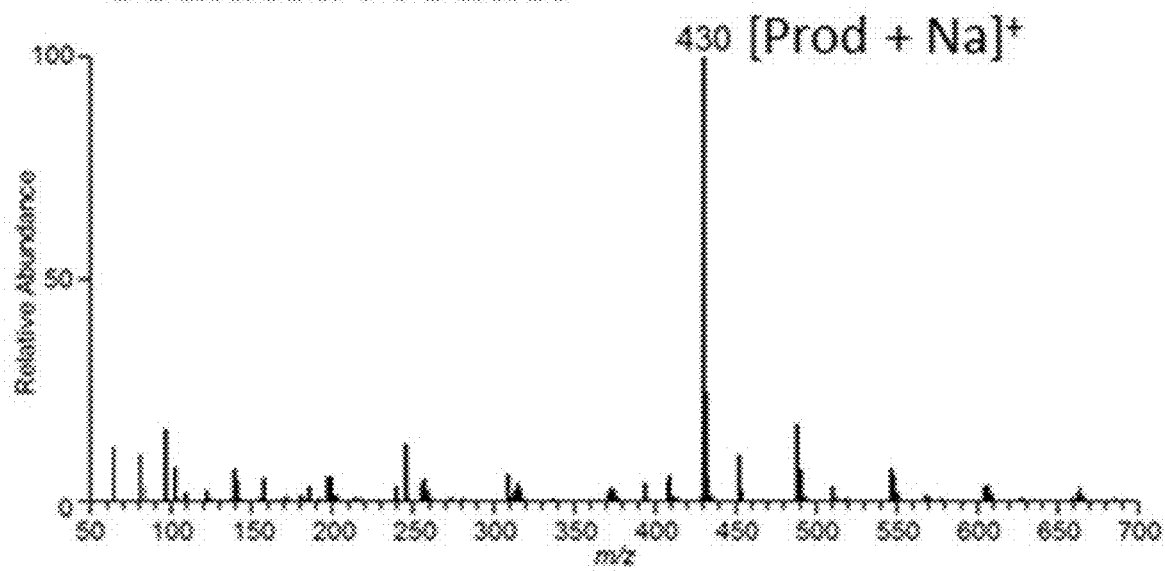

Protonated and sodiated species are commonly observed in electrospray ionization, where the adventitious sodium ions come from the walls of the glass capillary and from traces of salts in the system. Molecules with high proton affinity present only protonated ion forms such as L-Arg, whether in pure solution or in the reaction mixture (FIGS. 4A-B). For other compounds, however, the binding of a proton or sodium is affected by the presence of other molecules in the system. This can be seen in the MS spectrum of pure dipeptide Cbz-L-Val-L-Arg compared with that of Cbz-L-Val-L-Arg in the reaction mixture (FIGS. 6A-B). The change in ratio of protonated to sodiated ions has little influence in qualitative analysis, but such a change results in the complete failure of analyte quantitation unless there is a knowledge of the proportions of sodiated and protonated species. In such cases, the equilibrium was forced in favor of the protonated species by acidifying the solution (FIG. 6C). Sodiating the product has also been tried but it led to more byproducts being detected in the spectrum (FIG. 6D).

Figure 5A:
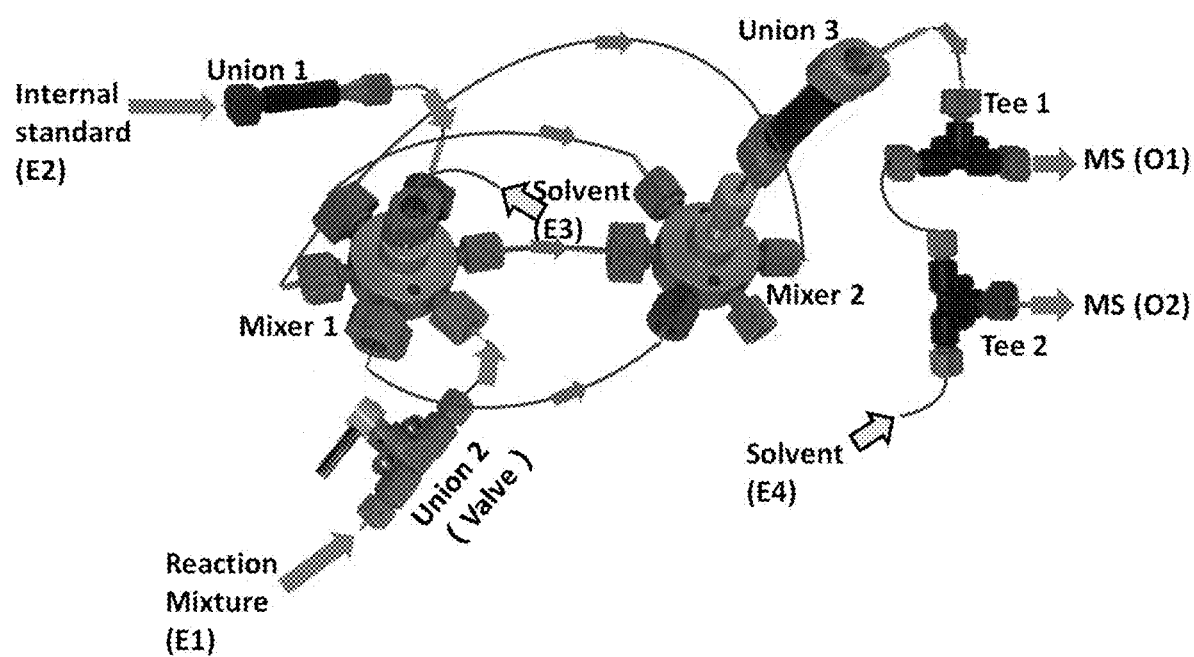
FIGS. 5A-B show evaluation of dead time for the quantitation device.
Figure 5B:
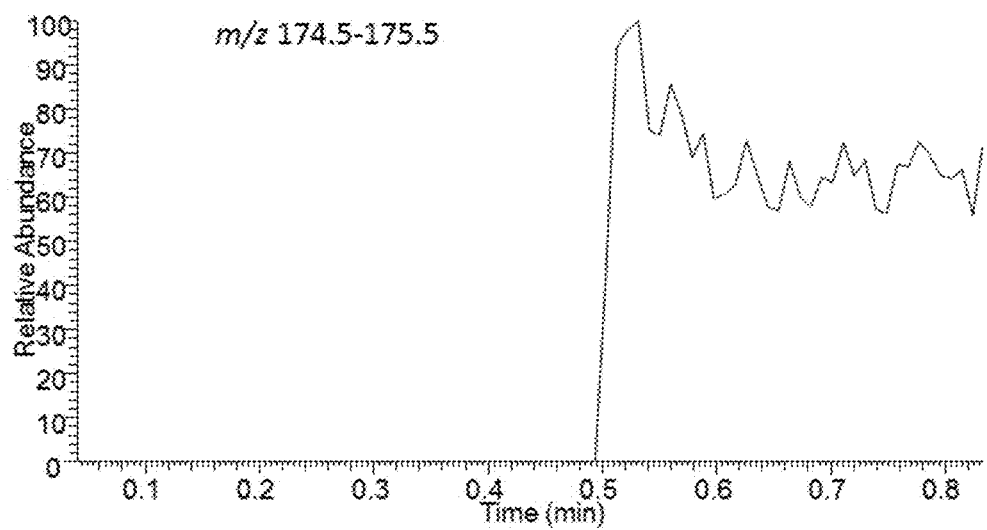

L-Arg-$^{13}C_6$ was used as internal standard for quantitation of both Cbz-L-Val-L-Arg as well as L-Arg, considering their structural similarities and the convenience of simultaneous quantitation of both analytes in the reaction mixture. A series of Cbz-L-Val-L-Arg solutions with known concentrations (15, 150, 1500, 15000, 150000 μM) and known L-Arg solutions (15, 150, 1500, 15000, 150000 μM) were introduced into the quantitation system separately and mixed with internal standard L-Arg-$^{13}C_6$ (13 mM) and diluted with ACN: $H_2O$ (v:v=1:1) at Mixer 1 and homogenized at Mixer 2 and union 3 (FIG. 5A). Samples were sprayed from two outlets (O1, O2) and ionized by applying a pulsed DC voltage at the emitters in turn. The intensity ratios of the analytes to those of the internal standards recorded in the SRM mode were plotted as a function of analyte concentration for each aliquot from the three outlets and they yielded excellent linear relationships at each outlet (FIGS. 4A-B).

Example 2

Synthetic arginine-rich peptides are efficient transporters of diverse biomolecules including nucleic acids, peptides, and proteins into the cytoplasmic and nuclei of living cells. As a result, arginine-containing peptides and conjugates show activity as therapeutic agents. A method to couple arginine (or Nω-nitroarginine) to the N-termini of amino acids and peptides using a benzotriazole derivative has been published. Katritzky, A. R.; Meher, G.; Narindoshvili, T. J. Org. Chem. 2008, 73, 7153-7158, incorporated herein by reference. The reaction of L-arginine with N-(Cbz-isopropyl-aminoacyl)-benzotriazole to provide Cbz-L-Val-L-Arg dipeptide (Scheme 1) was analyzed to test the performance of the present on-line monitoring apparatus.

Scheme 1. Reaction of L-arginine with N-(Cbz-isopropyl-aminoacyl)-benzotriazole to yield Cbz-L-Val-L-Arg

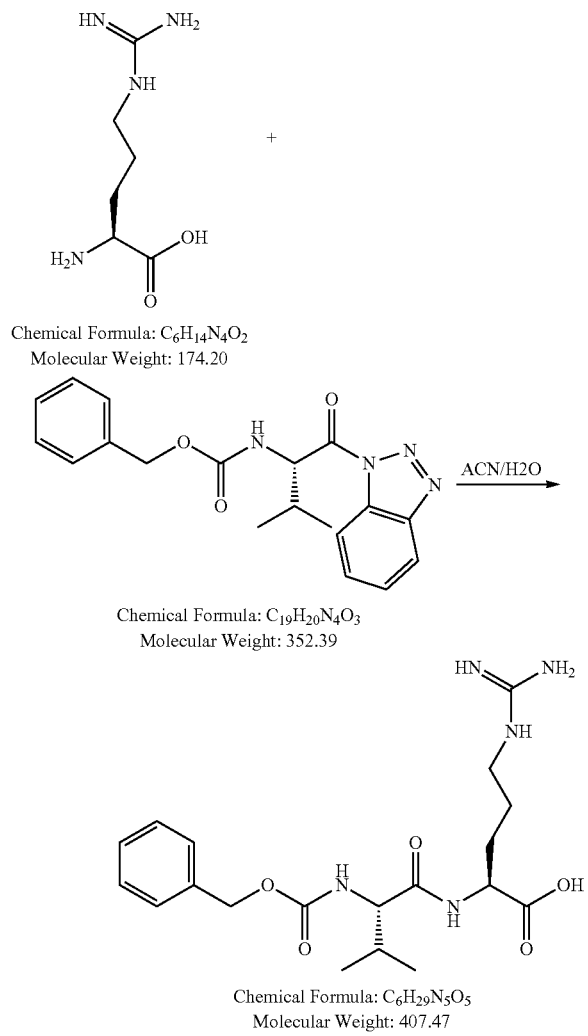

Figure 7A:
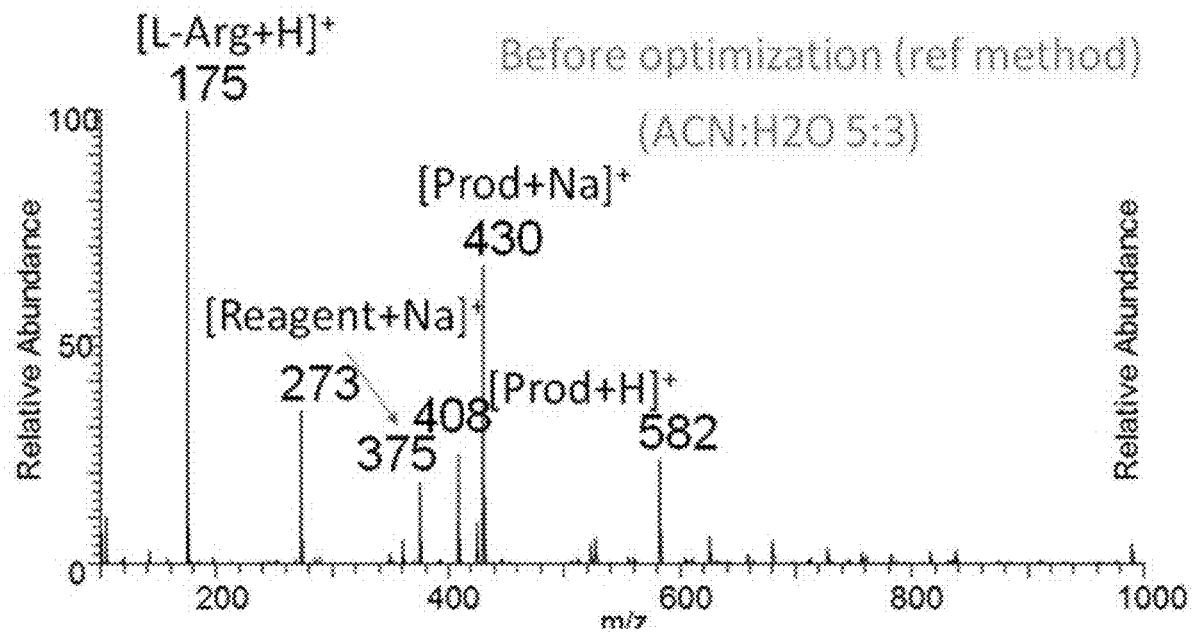
FIGS. 7A-C show mass spectra obtained after reaction for 1 hour under (FIG. 7A) reference condition.
Figure 7B:
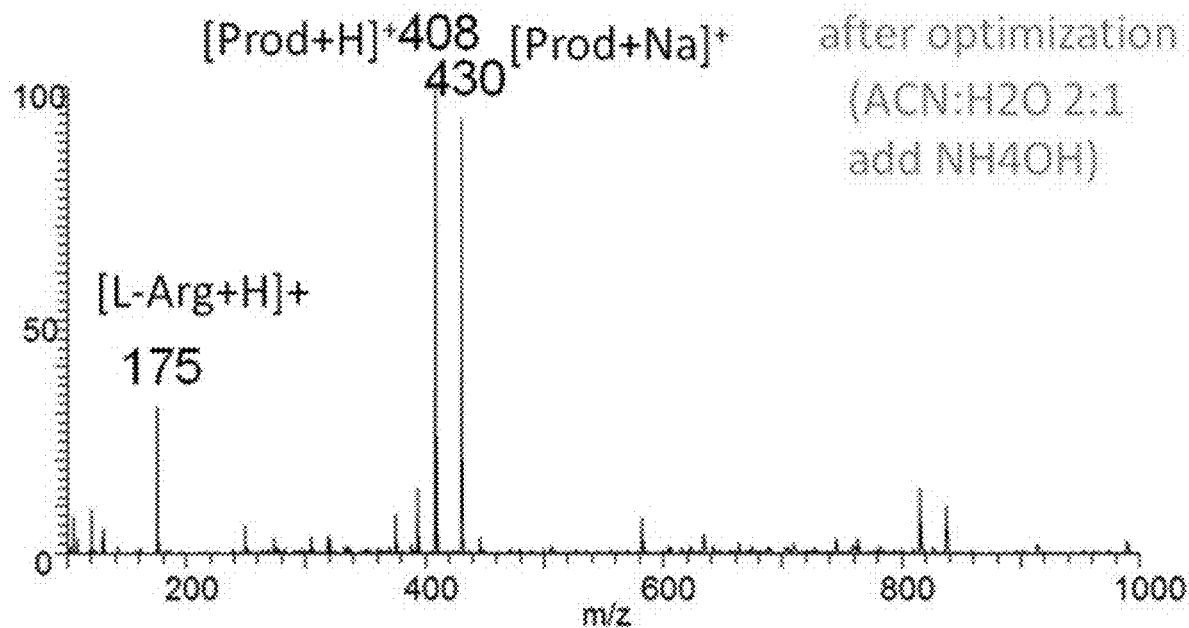
Figure 7C:
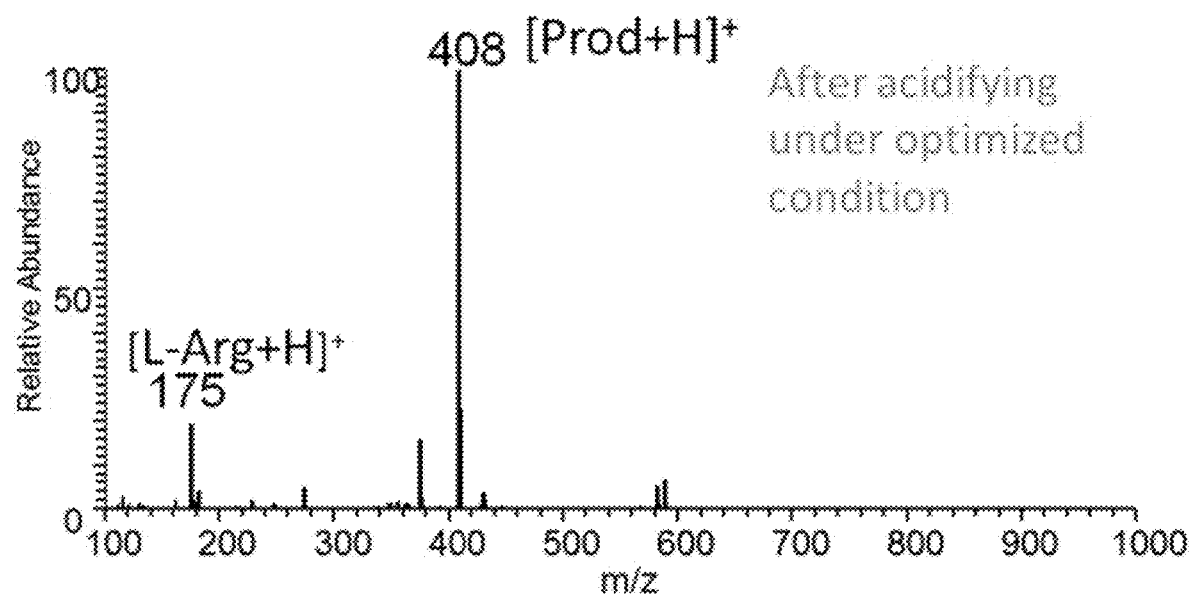

L-Arg and N-(Cbz-isopropyl-aminoacyl) benzotriazole, were mixed and suspended in ACN: H$_2$O (v:v 5:3). The reaction mixture was then continuously sampled at E1 (FIGS. 2A-B) at a flow rate of 30 μL/min. The dilution solvent ACN: H$_2$O (v:v 5:3) was infused at E2 at 30 μL/min and at E3 and E4 at a flow rate of 450 μL/min. The reaction was monitored by iESI-MS and the spectra recorded after 1 hour (FIG. 7A) showed protonated and sodiated products at m/z 408 and 430, while protonated L-Arg at m/z 175 was still the dominant peak in the spectrum. Adjusting the ratio of ACN and water to 2:1 (v:v) which dissolves both reagents, and adding catalytic amounts of ammonium hydroxide accelerated the reaction. With these changes, the product ions (m/z 408 and 430) showed a significant increase over the same 1 hour reaction time (FIG. 7B). The product ions now dominated the spectrum, while the reagent L-Arg had just 30% intensity relative to the protonated product. Spectra obtained after acidifying product is shown in FIG. 7C for comparison.

Figure 8:
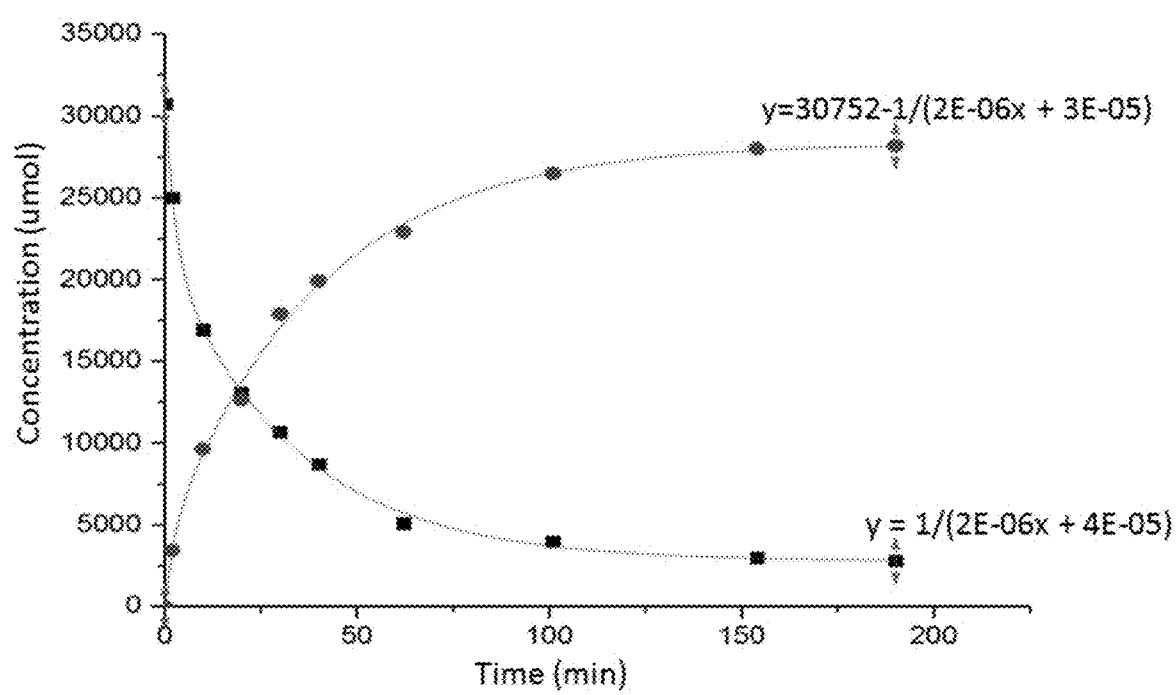
FIG. 8 shows kinetics of reaction of L-arginine with N-(Cbz-isopropyl-aminoacyl)-benzotriazole to yield Cbz-L-Val-L-Arg dipeptide using on-line MS quantitation device and monitoring both the disappearance of L-Arg and appearance of Cbz-L-Val-L-Arg. Equations fitted to the data are shown in the figure.
Figure 9:
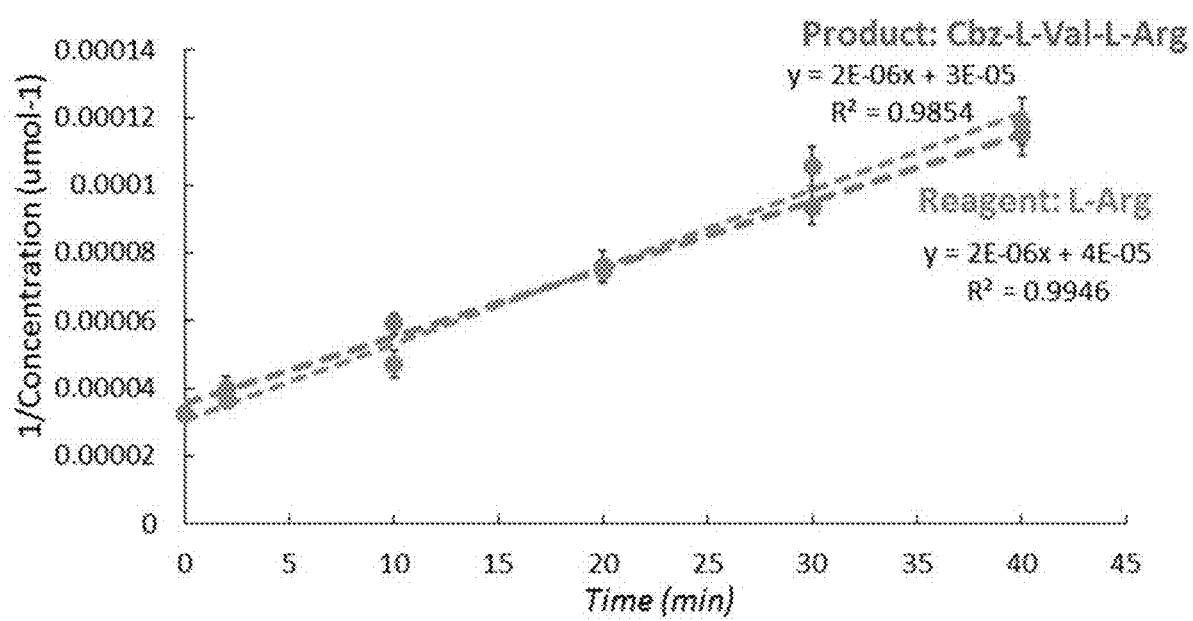
FIG. 9 is a graph showing the linear relationship of the reciprocal of concentration and time, showing the rate constant of dipeptide synthesis.

The reaction was then monitored quantitatively under the optimized reaction conditions (mild base) and monitored on-line using the on-line MS quantitation device under optimized monitoring conditions by infusing the internal standard L-Arg-$^{13}$C$_6$ and formic acid in ACN: H$_2$O (v:v, 2:1) solutions into the reaction mixture to give spectra of the type shown in FIG. 7C. The SRM transitions (m/z 175→158 for L-Arg), (m/z 408→347 for Cbz-L-Val-L-Arg) and (m/z 181→164 for L-Arg-$^{13}$C$_6$) were monitored using high frequency (10 Hz) switching between the two channels. The intensity ratios of the two transitions were averaged for a 10 second period. Conversion of the intensity to concentration was based on the calibration curve obtained above (FIGS. 4A-B). The concentration of L-Arg was plotted against the reaction time to construct a curve showing the reaction kinetics (FIG. 8). The inverse of concentration and time showed excellent linear relationships for both reagent and product (FIG. 9). The rate constant for this reaction was found to be 2 M$^{-1}$ min$^{-1}$ (see equations below).

$$-dc_{(L\text{-}Arg)}/dt = kc_{(L\text{-}Arg)} \times c_{(aminoacyl\ benzotriazole)} = kc^2_{(L\text{-}Arg)}$$

$$-dc_{(L\text{-}Arg)}/c_{(L\text{-}Arg)} = kc_{(L\text{-}Arg)}dt$$

$$(1/c_{(L\text{-}Arg)t}) - (1/c_{(L\text{-}Arg)0}) = kt$$

Example 3

The Wolff-Kishner reduction reaction was performed with various aldehydes and hydrazines for single and multi-sample reaction monitoring. Isatin and phenylhydrazine were reacted and immediately sampled for the next 2.5 hours. During this time, it was possible to observe the starting material, the hydrazone intermediate and the final product, as well as dimers and characteristic fragments. The reaction of isatin and hydrazine resulted in a similar outcome. After analyzing the reactions independently, both reactions were carried out and analyzed simultaneously. One immediate trade-off between single reaction monitoring and multiple reaction monitoring is the reduced time resolution as a function of the number of samples monitored (n).

Time resolution=20 seconds×$n$

Although the time resolution decreased by a factor of 2 (note, n=2), this was still adequate time and spectral resolution to observe all of the ions of interest as seen in the previous experiments. Upon successful analysis of two reactions, four reactions were run simultaneously. This was done with the addition of phenylhydrazine reacted with tolualdehyde and anisaldehyde. Using four CF-nESI probes the time resolution is approximately 80 seconds. This was still adequate time to monitoring reactions lasting for hours. To test the stability of the instrument, reaction mixtures were run for 12 hours with minimal contamination and little signal fluctuation.

Example 4

Figure 15:
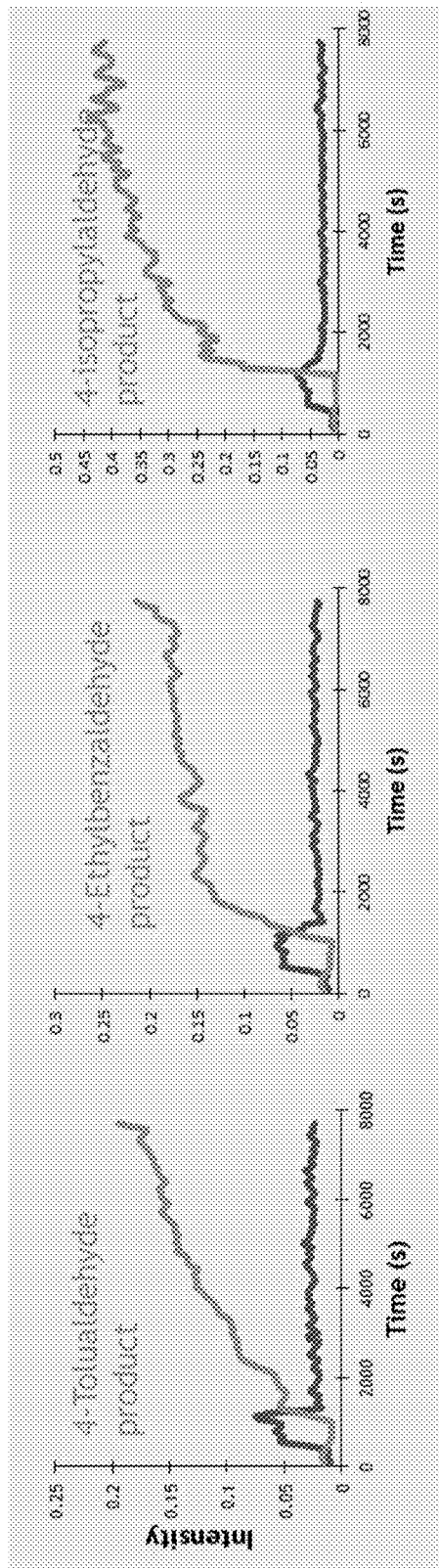
FIG. 15 shows monitoring of three reactions simultaneously.
Figure 16:
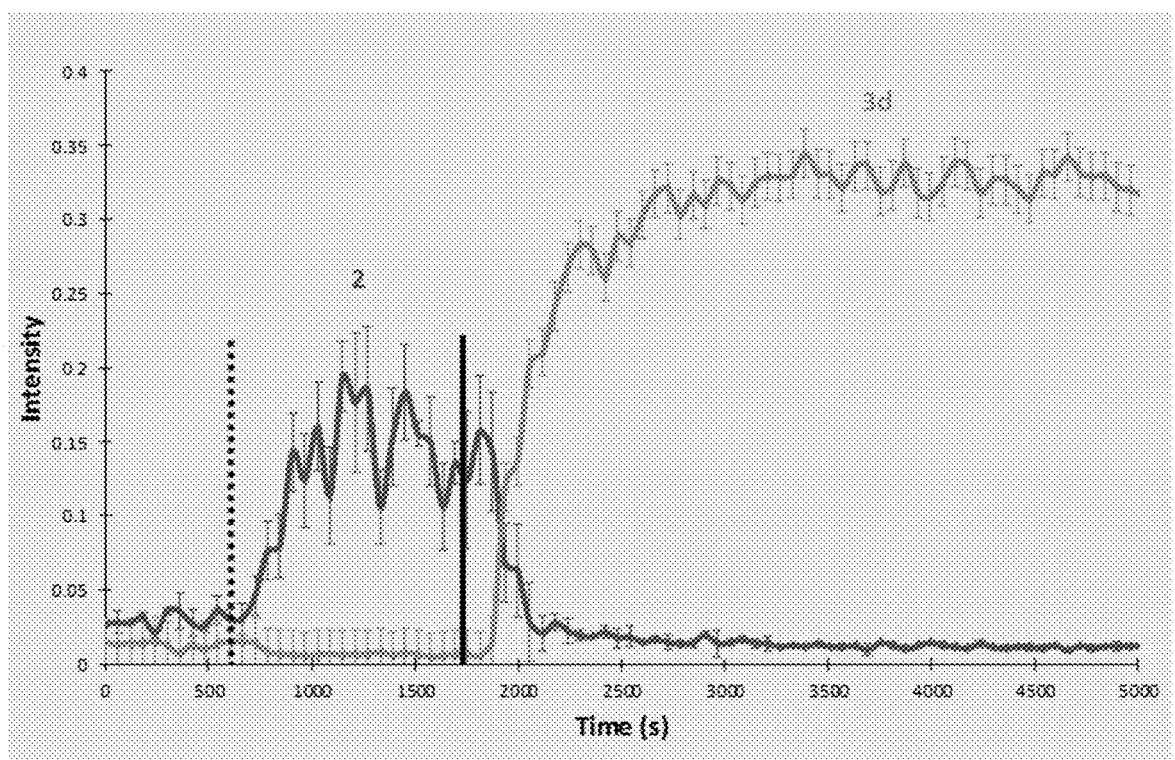
FIG. 16 is a graph showing variability between three ion generating devices within a single system for simultaneous reaction monitoring.

Systems of the invention were used to simultaneously monitor three reactions. FIG. 15 shows on-line and real-time generation of reaction product for each reaction. Using systems of the invention, six hours of data was collected in two hours. As shown in FIG. 16, there was little variability between ion generating devices.

Example 5

Figure 17:
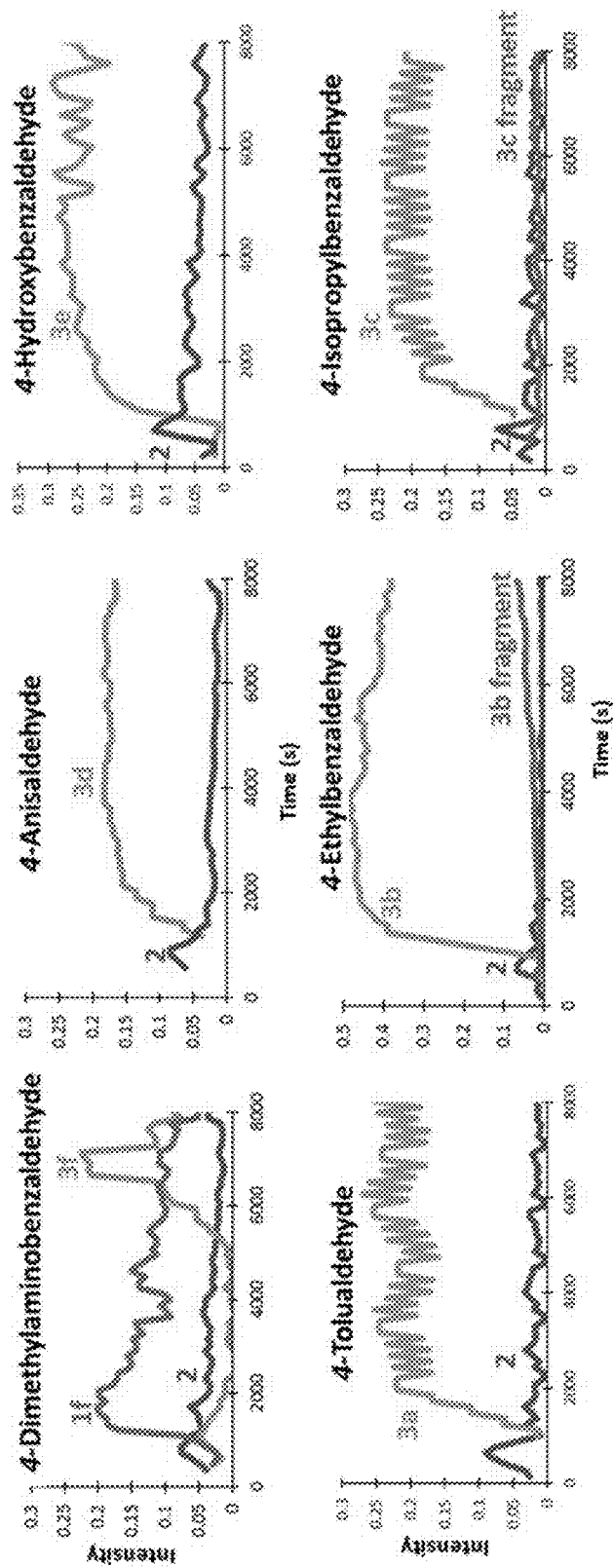
FIG. 17 shows monitoring of six reactions simultaneously.

Systems of the invention were used to simultaneously monitor six reactions. FIG. 17 shows on-line and real-time generation of reaction product for each reaction. Using systems of the invention, twelve hours of data was collected in two hours.

Example 6

As describe above, inductive electrospray ionization mass spectrometry may be used as the basis for an on-line quantitative reaction monitoring system which allows one to track and quantify chemical reactions in real time. A plug-in quantitation device can connect the reactor to the mass spectrometer and permit the accurate introduction of internal standards without affecting the reaction or later product separation. It also allows dilution of aliquots of the reaction solution by variable factors, so that the working concentration of each analyte falls within its linear dynamic range, facilitating accurate quantitation. The reaction of L-arginine with N-(Cbz-isopropyl-aminoacyl)-benzotriazole to yield the dipeptide Cbz-L-Val-L-Arg was successfully quantified using this system. The kinetics of the reaction are described below.

An on-line device based on inductive ESI-MS was designed and built to determine the concentrations of compounds of interest in reacting mixtures. The reaction of L-arginine and N-(Cbz-isopropyl-aminoacyl)-benzotriazole to yield a dipeptide Cbz-L-Val-L-Arg was monitored quantitatively as a proof-of-concept experiment. In the on-line quantitation system, small aliquots of the reaction mixture are taken, diluted to the extent needed, and mixed with known amounts of an appropriate internal standard (IS). Selected reaction monitoring (SRM) measurements are made on both the analyte and IS in the same solution. The entire operation, including sampling, dilution, and internal standard addition and SRM measurements, takes place within a minute or so and uses microliter volumes of reaction solution.

All reagents and solvents were of analytical grade or higher and were used directly without further purification. L-Arginine, L-Arg-13C6, N-(Cbz-isopropyl-aminoacyl)-benzotriazole, ammonium hydroxide and HPLC grade acetonitrile (ACN) and methanol (MeOH) were purchased from Sigma-Aldrich (St. Louis, Mo., USA). Water was purified and deionized using a Milli-Q system (Millipore, Bedford, Mass., USA).

Quantitative reaction monitoring was performed using a TSQ Quantum Access MAX (Thermo Scientific, San Jose, Calif.) in the multiple reaction monitoring (MRM) mode. Each monitoring experiment interrogated precursor/product ion pairs using narrow mass windows (m/z 0.010) for each ion for a period of 75 ms, repeated 20 times over a total of 1.5 s measurement time for each transition. Inlet capillary temperature and voltage were 300° C. and 35 V, respectively. The most abundant fragment was used for quantification.

Data were processed using the manufacturer's Xcalibur Quan Browser. Peaks were integrated, and quantification was performed using the ratio of the areas under the curves for the analyte and internal standard. Trend lines were constructed using linear least-squares.

Synthesis of Dipeptide Cbz-L-Val-L-Arg as its quantitation standard: N-(Cbz-isopropyl-aminoacyl)-benzotriazole (172.5 mg, 0.5 mmol) was added at 20° C. to a solution of L-arginine (85.05 mg, 0.5 mmol) in ACN (10 mL)/H2O (5 mL). The reaction mixture was then stirred at 20° C. until the starting material was completely consumed as observed by MS. After addition of 4 N HCl (1 mL), the solution was concentrated under reduced pressure to remove ACN. The residue was extracted with EtOAc (20 mL), and the organic extract was washed with 4 N HCl (5 mL) and saturated NaCl (10 mL) and then dried over anhydrous MgSO4. Evaporation of the solvent gave the desired product arginine-valine dipeptide in pure form, which was recrystallized from MeOH/Et2O.

Figure 18:
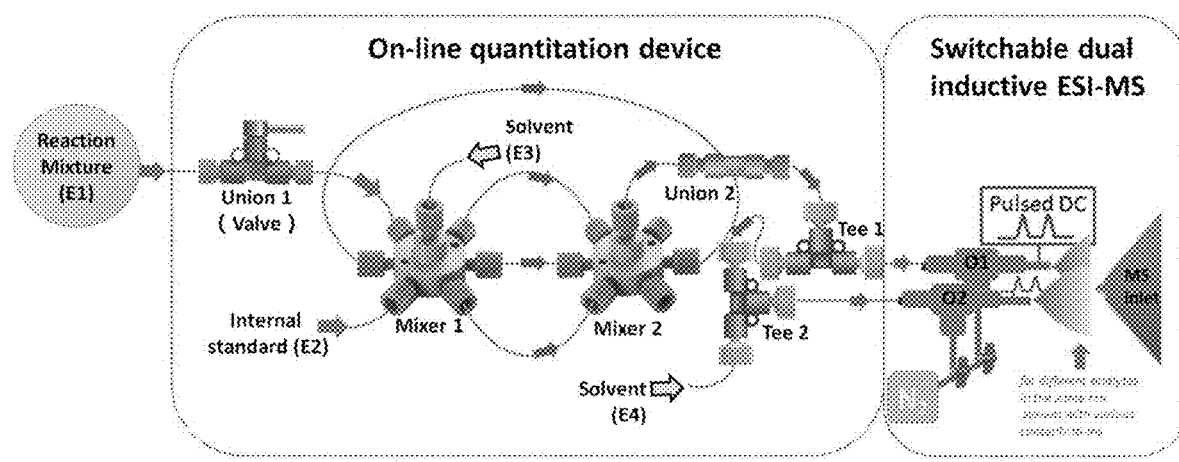
FIG. 18 shows an on-line reaction monitoring quantitation system with switchable dual inductive ESI MS.

Referring to the system illustrated in FIG. 18, the reagents were mixed with solvent in the syringe and was pressurized at E1 by syringe pump at a flow rate of 15 μL/min to transfer it through the on-line quantitation device to the emitter-spray tip of the inductive ESI. Six junctions were used in the quantitative monitoring device: two unions, two 7-port mixers and 2 tees. IS was introduced at E2 at a flow rate of 15 μL/min, while dilution solvent was pumped at a flow rate of 450 μL/min at E3 and E4 The capillaries used in the system were silica-coated glass capillary with i.d. 100 μm except the one that connects mixer 2 with union 2 whose i.d. was 530 μm. A tee was added at the front of the capillary tip to introduce sheath gas. A home-built power supply provided a positive pulsed output of 860 V at 2000 Hz which was supplied to an electrode that surrounded but did not make physical contact with the sheath gas line. Strong electric fields were produced in the solution inside the emitter and they gave rise to a spray of droplets. This procedure resulted in the pulsed emission of charged analytes from the reaction solution at a controlled pulse rate 2000 Hz. The fact that the capillary did not block even with concentrated reaction solutions is ascribed to self-cleaning associated with the rapid forward and reverse potentials experienced in the solution during to ringing of the inductive circuit.

Turning back to the exemplary embodiment, as the reaction mixture, internal standard and large flow of spray solvent converge at mixer 1, the increased pressure is released by four outlets of mixer 1 and converge again in mixer 2 with outlet capillary of larger ID (530 um). The design also disrupts the laminar flow and greatly enhances the mixing of three different compounds. Union 3 helps further mixing and completes in a uniform solution. In this device, two outlets (O1 and O2) are provided, each subjecting the reaction mixture to a different dilution factor, and each connected to a separate iESI emitter to provide on-line quantitation of analytes present over particular ranges of concentrations.

A solution of L-Arg (100 μM) was prepared in ACN: $H_2O$ (v:v=2:1), injected at E1 and mixed with an equal amount of solvent (ACN: H2O, v:v=2:1) injected at E2. The same solvent was infused simultaneously at E3 and E4. Samples were collected from outlets 1, 2, (O1, O2), mixed with internal standard L-Arg-13C6 (50 μM) and analyzed by iESI-MS. Based on the off-line calibration curve recorded for L-Arg, the concentrations of L-Arg after dilution were determined. With fixed capillary IDs, angles and positions of the tees, the dilution factor is related to the pressure (hence flow rate) at E1-E4.

The device produced different dilution factors at each outlet, which allows compatibility of samples with different concentrations in one mixture using dilution factors that cause their concentrations to fall to within their linear dynamic ranges for each chosen sprayer (and hence dilution factor) and so optimize quantification by MS. The optimized conditions were found when using a flow rate of 30 μL/min for E1 and E2, 450 μL/min for E3 and E4, they corresponding to 17 times dilution at O1, 255 times dilution at O2. The experiment with optimized conditions was repeated five times and showed 8% variance. The variation between each batch could be reduced by fixing the configuration of the device. O2 has the higher dilution factor which makes it useful for quantitation of concentrated compounds (e.g. reagents at the beginning of a reaction and products at the end of a reaction), while O1 with the lower dilution factor meets the needs of quantitation of less concentrated compounds (products at the beginning and reagents at the end, and trace intermediates or impurities). Volumes were also measured for each sample and flow rates were calculated at each outlet.

The system dead time can be defined as the lag between the status of the bulk-phase reaction and the time of subsequent mass analysis. L-Arg was injected into E1, while solvent (HCN:H2O, v:v=2:1) was added through E2, E3 and E4. The dead time was found to be 20 s at O1, and 30 s at O2, as evaluated by observing the time before the emergence of L-Arg in the full mass scan (shown in form of ion chronogram). The dead time suggests that after switching the emitters 30 s delay is required before collection of data for the next time point.

In the inductive ESI-MS system based on-line reaction quantitative monitoring as shown in FIG. 18, the reaction solution is pressurized to transfer through the on-line quantitation unit via capillaries and junctions to the selected emitter-spray tip, where a positive potential is pulsed repeatedly to produce transient strong electric fields in the spray solution resulting in emission of bursts of charged droplets. Considering that reactant, intermediate and product concentrations will vary greatly over the course of a synthesis, two spray emitters were provided, each subjecting the reaction mixture to a different dilution factor, and each connected to a separate inductive ESI emitter to provide on-line quantitation of analytes present over particular ranges of concentrations. Sheath gas was used to aid in the nebulization process, to minimize variations in droplet size and to protect the nebulized reaction mixture from the atmosphere.

The designed quantitation unit was composed of six junctions: union 1 being used as a valve to control the introduction of reaction solution, mixer 1, 2 and union 2 for mixing of internal standard, formic acid (to remove sodiated product ion, to be discussed later) into the reaction solution and spray solvent, tee 1 is used to split the working solution to the MS inlet and tee 2 for further dilution with spray solvent. Two sprayers were connected with tee 1 and tee 2 and their positions were fixed to allow both spray plume to reach MS inlet. The plume was switched by controlling the valves of sheath gas.

The designed quantitation unit is able to reach fast mixing of reaction solution, IS and dilution solvent. Mixing to what extent decides the dilution factors for each outlet which can influence the accuracy of quantitation. The largest Reynolds Number of this system was 21. In order to disrupt the laminar flow in the capillaries, this system used passive micromixers (two 7-port mixers and one union) which do not require external energy and rely entirely on diffusion or chaotic advection via contacting, decrease of diffusion path, and injection of substreams.

As the reaction mixture/internal standard solution passes through T2-T4 (FIG. 18), an increase/decrease in the fluid flow speed occurs with the decrease/increase in pressure caused by changes in the capillary ID. To balance the pressure and achieve the required flow direction, pressures at the four inlets (E1-E4, blue arrows, FIG. 18) need to be balanced by adjusting the solvent flow rate.

L-Arginine and L-arginine-$^{13}C_6$ were chosen as the model analyte and IS to evaluate the dilution factors for the two outlets. The pair L-Arg and L-Arg-$^{13}C_6$ was found to give a linear dynamic range of 5 nM-500 μM ($10^5$) in ACN: H$_2$O (v:v=2:1) using the SRM transitions (m/z 175→158 and 181→164).

A solution of L-Arg (100 μM) was prepared in ACN: H$_2$O (v:v=2:1), injected at E1 (FIG. 18) and mixed with an equal amount of solvent (ACN: H$_2$O, v:v=2:1) injected at E2. The same solvent was infused simultaneously at E3 and E4. Samples were collected from outlets 1, 2, 3 (O1 and O2 in FIG. 18, O3 not shown), mixed with internal standard L-Arg-$^{13}C_6$ (50 μM) and analyzed by iESI-MS. Based on the off-line calibration curve recorded for L-Arg, the concentrations of L-Arg after dilution were determined. With fixed capillary IDs, angles and positions of the tees, the dilution factor is related to the pressure (hence flow rate) at E1-E4.

Figure 19:
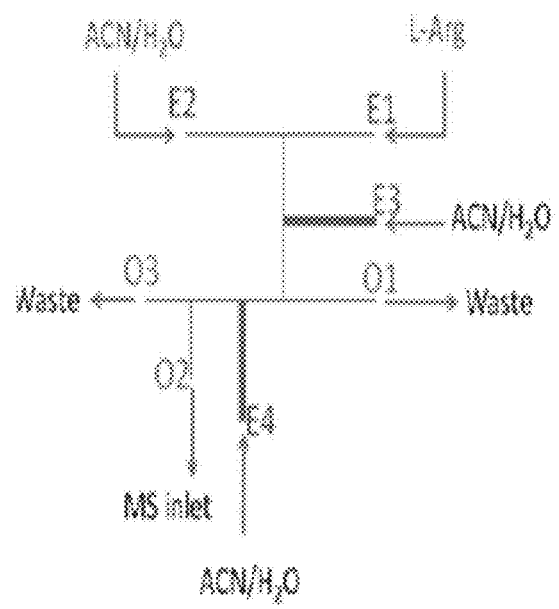
FIG. 19 shows an on-line reaction monitoring quantitation system having 3 outlets and set up for determining lag between the status of a bulk-phase reaction and the time of subsequent mass analysis.

The device produced different dilution factors at each outlet, which allows compatibility of samples with different concentrations in one mixture using dilution factors that cause their concentrations to fall to within their linear dynamic ranges for each chosen sprayer (and hence dilution factor) and so optimize quantification by MS. The optimized conditions were found when using a flow rate of 15 μL/min for E1, 300 μL/min for E2 and E3, they corresponding to 18 times dilution at O1, 120 times dilution at O2 and 250 times dilution at O3 (dilution at O1 and O2 are shown by the labelled dots in FIG. 19). The experiment with optimized conditions was repeated five times and showed 11% variance. The variation may be further reduced by providing a fixed configuration for the device. Among the three outlets, O3 (not shown) has the highest dilution factor which makes it useful for quantitation of concentrated compounds (e.g. reagents at the beginning of a reaction and products at the end of a reaction), while O1 with the lowest dilution factor meets the needs of quantitation of less concentrated compounds (products at the beginning and reagents at the end, and trace intermediates or impurities). Volumes were also measured for each sample and flow rates were calculated at each outlet.

Figure 20:
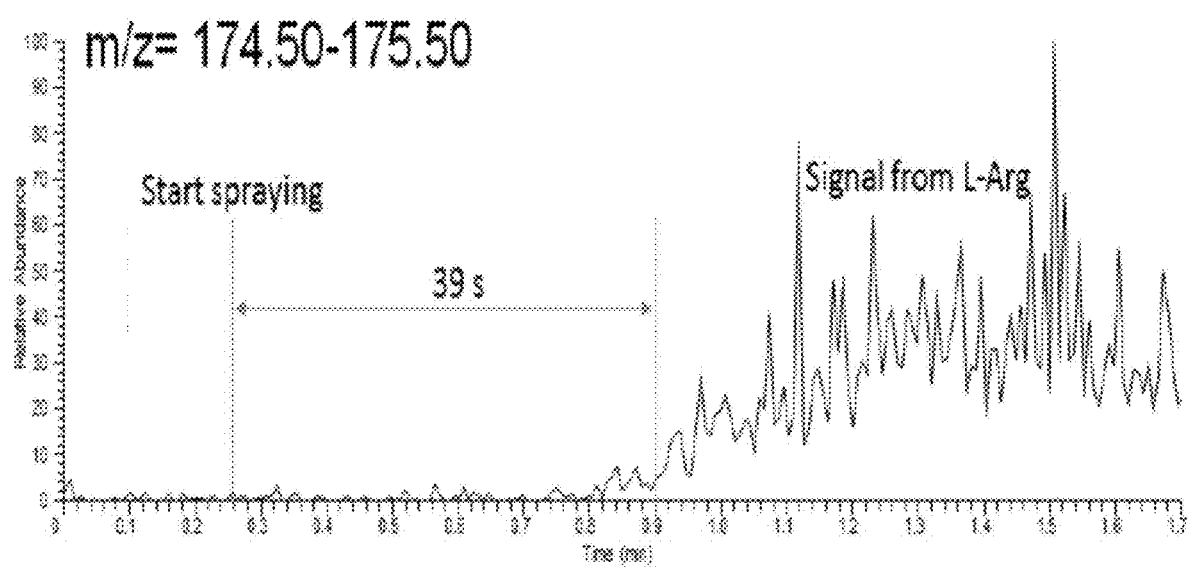
FIG. 20 shows an ion chronogram obtained using the system in FIG. 19 to determine dead time

The system dead time can be defined as the lag between the status of the bulk-phase reaction and the time of subsequent mass analysis. L-Arg was injected into E1 (FIG. 19), while solvent (HCN:H2O, v:v=2:1) was added through E2, E3 and E4. The dead time was found to be 20 s at O1, 39 s at O2 and 40 s at O3, as evaluated by observing the time before the emergence of L-Arg in the full mass scan (shown in its ion chronogram, FIG. 20). The dead time suggests that after switching the emitters 40 s delay is required before collection of data for the next time point.

Protonated and sodiated species are commonly observed in electrospray ionization, where the adventitious sodium ions come from the walls of the glass capillary and from traces of salts in the system. Molecules with high proton affinity present only protonated ion forms such as L-Arg, whether in pure solution or in the reaction mixture. For other compounds, however, the binding of a proton or sodium is affected by the presence of other molecules in the system. This can be seen in the MS spectrum of pure dipeptide Cbz-L-Val-L-Arg compared with that of Cbz-L-Val-L-Arg in the reaction mixture. The ratio change of protonated to sodiated ions has little influence in qualitative analysis, but such a change results in the complete failure of analyte quantitation unless there is a knowledge of the proportions of sodiated and protonated species. In such cases, we choose to force the equilibrium in favor of the protonated species by acidifying the solution. Sodiating the product has also been tried but it led to more byproducts being detected in the spectrum.

L-Arg-13C6 was used as internal standard for quantitation of both Cbz-L-Val-L-Arg as well as L-Arg, considering their structural similarities and the convenience of simultaneous quantitation of both analytes in the reaction mixture. A series of Cbz-L-Val-L-Arg solutions with known concentrations (15, 150, 1500, 15000, 150000 μM) and known L-Arg solutions (15, 150, 1500, 15000, 150000 μM) were introduced into the quantitation system separately and mixed with internal standard L-Arg-13C6 (13 mM) at T1, then diluted with ACN: $H_2O$ (v:v=1:1) at T2 and T4 (FIG. 18). Samples were sprayed from three outlets (O1-O3, O3 not shown) and ionized by applying a pulsed DC voltage at the emitters in turn. The intensity ratios of the analytes to those of the internal standards recorded in the SRM mode were plotted as a function of analyte concentration for each aliquot from the three outlets and they yielded excellent linear relationships at each outlet.

What is claimed is:

1. A reaction monitoring system, the system comprising:
   a reaction vessel comprising an outlet;
   a quantitation unit coupled to the outlet and configured to introduce internal standard and solvent into a reaction mixture flowed from the reaction vessel, wherein the quantitation unit comprises:
      a first mixer in fluid communication with the outlet and an internal standard reservoir and operable to receive reaction mixture and internal standard respectively therefrom;
      a second mixer in fluid communication with the first mixer and operable to receive mixed reaction mixture and internal standard therefrom;
   a third mixer after the quantitation unit and in fluid communication with the second mixture, the third mixer comprising a first inlet that receives fluid flow from the second mixer, a second inlet that receives a spray solvent and an outlet;
   one or more ion generating devices in fluid communication with the third mixer and operable to receive flow therefrom via one or more channels; and
   a mass spectrometer that receives ions from the one or more ion generating devices.

2. The system according to claim 1, wherein the mixer comprises a plurality of inlets and a union, wherein one of a plurality of inlets of the first mixer is coupled to the reaction vessel, another of the plurality of inlets of the first mixer is connected to the internal standard reservoir, and one or more outlets of the first mixer is coupled to the second mixer of the one or more mixers, which comprises one or more outlets that couple to the one or more ion generating devices.

3. The system according to claim 2, wherein the second mixer comprises one or more outlets operably coupled to two ion generating devices.

4. The system according to claim 3, wherein each ion generating device is configured for inductive charging electrospray ionization.

5. The system of claim 3, wherein one of the two ion generating devices is in fluid communication with a solvent reservoir and operable to receive additional solvent to dilute, relative to the other ion generation device, the mixed reaction mixture and internal standard.

6. The system according to claim 1, wherein the one or more ion generating devices are coupled to an actuator, the system further comprising:
   one or more additional reaction vessels, each operably associated with an additional ion generating device coupled to the actuator,
   wherein the actuator is configured to allow movement of the one or more ion generating devices and each additional ion generating device relative to the mass spectrometer.

7. The system of claim 1, wherein the first mixer is in fluid communication with a solvent source and operable to receive solvent therefrom.

8. A system for quantifying multiple reactions, the system comprising:
   a plurality of reaction vessels, each comprising an outlet;
   a plurality of quantitation units each coupled to one of the outlets and configured to introduce internal standard and solvent into reaction solution flowed from one of the plurality of reaction vessels, wherein each of the plurality of quantitation units comprises a first mixer for receiving reaction solution, solvent, and internal standard and a second mixer for receiving the mixed reaction solution, solvent, and internal standard from the first mixer;
   a plurality of third mixers, each coupled after each of the plurality of quantitation units to one of the outlets of the second mixers and in fluid communication with the second mixture of each of the plurality of quantitation units, each of the plurality of third mixers comprising a first inlet that receives fluid flow from the second mixer, a second inlet that receives a spray solvent and an outlet;
   one or more ion generating devices for each of the plurality of quantitation units, the one or more ion generating devices each configured to receive flow from its associated third mixer of the plurality of third mixers via one or more channels connecting between each of the plurality of quantitation units and the one or more ion generating devices;
   a mass spectrometer that receives ions from the one or more ion generating devices; and
   an actuator coupled to the one or more ion generating devices for each of the plurality of quantitation units to thereby allow movement of the one or more ion generating devices for each of the plurality of quantitation units relative to the mass spectrometer.

9. The system according to claim 8, wherein the one or more ion generating devices for each of the plurality of quantitation units are nano-electrospray ionization probes.

10. The system according to claim 9, wherein the actuator comprises a rotary stage that holds each of the one or more ion generating devices for each of the plurality of quantitation units, and
   wherein the actuator further comprises an electrode positioned proximate the rotary stage to impart an electric charge to each of the one or more ion generating devices for each of the plurality of quantitation units as the one or more ion generating devices for each of the plurality of quantitation units rotate past the electrode.

* * * * *